(12) United States Patent
Sorge

(10) Patent No.: US 8,263,338 B2
(45) Date of Patent: *Sep. 11, 2012

(54) METHODS OF ENRICHING FOR AND IDENTIFYING POLYMORPHISMS

(75) Inventor: Joseph A. Sorge, Wilson, WY (US)

(73) Assignee: Catalyst Assets LLC, Jackson, WY (US)

( * ) Notice: Subject to any disclaimer, the term of this patent is extended or adjusted under 35 U.S.C. 154(b) by 875 days.

This patent is subject to a terminal disclaimer.

(21) Appl. No.: 11/786,204

(22) Filed: Apr. 11, 2007

(65) Prior Publication Data
US 2007/0248979 A1 Oct. 25, 2007

Related U.S. Application Data

(60) Division of application No. 10/391,090, filed on Mar. 18, 2003, which is a continuation of application No. 09/338,855, filed on Jun. 23, 1999, now abandoned.

(51) Int. Cl.
*C12Q 1/68* (2006.01)
(52) U.S. Cl. .................... 435/6.12; 435/6.1
(58) Field of Classification Search ................... None
See application file for complete search history.

(56) References Cited

U.S. PATENT DOCUMENTS

| | | | |
|---|---|---|---|
| 4,656,127 A | 4/1987 | Mundy | 435/6 |
| 4,883,750 A | 11/1989 | Whiteley et al. | 435/6 |
| 4,988,617 A | 1/1991 | Landegren et al. | 435/6 |
| 5,227,292 A | 7/1993 | White et al. | |
| 5,234,811 A | 8/1993 | Beutler et al. | |
| 5,283,174 A | 2/1994 | Arnold et al. | 435/6 |
| 5,376,526 A | 12/1994 | Brown et al. | 435/6 |
| 5,427,930 A | 6/1995 | Birkenmeyer et al. | 435/91.52 |
| 5,451,502 A | 9/1995 | George, Jr. | |
| 5,470,705 A | 11/1995 | Grossman et al. | 435/6 |
| 5,487,985 A | 1/1996 | McClelland et al. | |
| 5,494,810 A | 2/1996 | Barany et al. | 435/91.52 |
| 5,501,964 A | 3/1996 | Wigler et al. | 435/91.2 |
| 5,518,901 A * | 5/1996 | Murtagh | 435/91.2 |
| 5,571,672 A | 11/1996 | Slavicek et al. | 435/6 |
| 5,589,330 A * | 12/1996 | Shuber | 435/5 |
| 5,599,696 A | 2/1997 | Mueller et al. | 435/91.2 |
| 5,604,099 A | 2/1997 | Erlich et al. | 435/6 |
| 5,679,524 A | 10/1997 | Nikiforov et al. | 435/6 |
| 5,716,785 A | 2/1998 | Van Gelder et al. | 435/6 |
| 5,744,311 A | 4/1998 | Fraiser et al. | 435/6 |
| 5,759,780 A * | 6/1998 | Parker et al. | 435/6.14 |
| 5,763,168 A | 6/1998 | Lalouel et al. | |
| 5,780,231 A | 7/1998 | Brenner | |
| 5,795,976 A | 8/1998 | Oefner et al. | 536/25.6 |
| 5,811,269 A | 9/1998 | Nadeau et al. | 435/91.1 |
| 5,849,486 A | 12/1998 | Heller et al. | |
| 5,858,656 A | 1/1999 | Deugau et al. | 435/6 |
| 5,866,429 A | 2/1999 | Bloch | 436/94 |
| 5,869,252 A | 2/1999 | Bouma et al. | 435/6 |
| 5,874,215 A | 2/1999 | Kuiper et al. | 435/6 |
| 5,891,627 A | 4/1999 | Evans et al. | 435/6 |
| 5,891,636 A | 4/1999 | Van Gelder et al. | 435/6 |
| 5,994,068 A | 11/1999 | Guilfoyle et al. | 435/6 |
| 6,027,889 A | 2/2000 | Barany et al. | 435/6 |
| 6,033,861 A | 3/2000 | Schafer et al. | |
| 6,045,994 A | 4/2000 | Zabeau et al. | 435/6 |
| 6,130,073 A | 10/2000 | Eggerding | 435/91.2 |
| 6,210,891 B1 * | 4/2001 | Nyren et al. | 435/6.12 |
| 6,280,941 B1 | 8/2001 | Tsao et al. | |
| 6,287,825 B1 | 9/2001 | Weissman et al. | 435/91.2 |
| 6,309,824 B1 * | 10/2001 | Drmanac | 435/6.11 |
| 6,322,968 B1 | 11/2001 | Head et al. | |
| 6,361,947 B1 | 3/2002 | Dong et al. | |
| 6,495,319 B1 | 12/2002 | McClelland et al. | 435/6 |
| 6,506,594 B1 | 1/2003 | Barany et al. | 435/287.2 |
| 6,534,293 B1 | 3/2003 | Barany et al. | 435/91.2 |
| 6,703,228 B1 * | 3/2004 | Landers et al. | 435/91.2 |

FOREIGN PATENT DOCUMENTS

| | | |
|---|---|---|
| FR | 2650840 | 2/1991 |
| WO | WO91/02087 | 2/1991 |
| WO | WO92/15712 | 9/1992 |

OTHER PUBLICATIONS

Kohsaka, Hitoshi et al. Solid Phase Polymerase Chain Reaction. Journal of Clinical Laboratory Analysis 1994 vol. 8 pp. 452-455.*
Kinzler, et al., "Whole genome PCR: application to the identification of sequences bound by gene regulatory proteins," Nucleic Acids Research (1989), vol. 17, No. 10, pp. 3645-3653.

(Continued)

*Primary Examiner* — James Martinell
(74) *Attorney, Agent, or Firm* — Eric P. Mirabel; Kathleen Williams

(57) ABSTRACT

The invention encompasses methods for enriching for and identifying a polymorphism within a nucleic acid sample either by separating a subset of a nucleic acid sample or by selectively replicating a subset of a nucleic acid sample such that the polymorphism is contained within a nucleic acid population with reduced complexity, and then identifying the polymorphism within the enriched nucleic acid sample. Methods also are disclosed for enriching for and identifying a polymorphism by contacting a nucleic acid sample that includes a subset of nucleic acid molecules having a sequence that binds to a sequence-specific binding activity with a molecule having a sequence-specific binding activity under conditions which permit specific binding, such that the subset of nucleic acid molecules bound to the activity is enriched for nucleic acid molecules having the sequence recognized by the sequence-specific binding activity, and detecting a polymorphism with respect to a reference sequence in the subset of nucleic acid molecules.

28 Claims, No Drawings

OTHER PUBLICATIONS

Lucito, et al., "Genetic analysis using genomic representations," Proc. Natl. Acad. Sci USA (1998), vol. 95, pp. 4487-4492.

Landegren, et al., "A Ligase-Mediated Gene Detection Technique," Science (1988), vol. 241, pp. 1077-1080.

Nickerson, et al., "Automated DNA diagnostics using an ELISA-based oligonucleotide ligation assay," Proc. Natl. Acad. Sci. USA (1990), vol. 87, pp. 8923-8927.

Grossman, et al., "High-density multiplex detection of nucleic acid sequences: oligonucleotide ligation assay and sequence-coded separation," Nucleic Acids Research (1994), vol. 22, No. 21, pp. 4527-4534.

Eggerding, "A One-step Coupled Amplification and Oligonucleotide Ligation Procedure for Multiplex Genetic Typing," PCR Methods and Applications (1995), vol. 4, pp. 337-345.

Eggerding, et al., "Fluorescence-Based Oligonucleotide Ligation Assay for Analysis of Cystic Fibrosis Transmembrane Conductance Regulator Gene Mutations," Human Mutation (1995), vol. 5, pp. 153-165.

Tobe, et al., "Single-well genotyping of diallelic sequence variations by a two-color ELISA-based oligonucleotide ligation assay," Nucleic Acids Research (1996), vol. 24, No. 19, pp. 3728-3732.

Barany, "Genetic disease detection and DNA amplification using cloned thermostable ligase," Proc. Natl. Acad. Sci. USA (1991), vol. 88, pp. 189-193.

Khanna, et al., "Multiplex PCR/LDR for detection of K-*ras* mutations in primary colon tumors," Oncogene (1999), vol. 18, pp. 27-38.

Shafer, et al., "Interlaboratory Comparison of Sequence-Specific PCR and Ligase Detection Reaction to Detect a Human Immunodeficiency Virus Type 1 Drug Resistance Mutation," Journal of Clinical Microbiology (1996), vol. 34, No. 7, pp. 1849-1853.

Kälin, et al., "Evaluation of the ligase chain reaction (LCR) for the detection of point mutations," Mutation Research (1992), vol. 283, pp. 119-123.

Pfeffer, et al., "A ligase chain reaction targeting two adjacent nucleotides allows the differentiation of cowpox virus from other *Orthopoxvirus* species," Journal of Virological Methods (1994), vol. 49, pp. 353-360.

Wiedmann, et al., "Detection of *Listeria monocytogenes* with a Nonisotopic Polymerase Chain Reaction-Coupled Ligase Chain Reaction Assay," App. and Environ. Microbiology (1993), vol. 59, No. 8, pp. 2743-2745.

Mueller, et al., "In Vivo Footprinting of a Muscle Specific Enhancer by Ligation Mediated PCR," Science (1989), vol. 246, pp. 780-786.

Smith, "Ligation-mediated PCR of Restriction Fragments from Large DNA Molecules," PCR Methods and Applications (1992), vol. 2, pp. 21-27.

Unrau, et al., "Non-cloning amplification of specific DNA fragments from whole genomic DNA digests using DNA 'indexers'," Gene (1994), vol. 145, pp. 163-169.

Guilfoyle, et al., "Ligation-mediated PCR amplification of specific fragments from a Class-II restriction endonuclease total digest," Nucleic Acids Research (1997), vol. 25, No. 9, pp. 1854-1858.

Vos, et al, "AFLP: a new technique for DNA fingerprinting," Nucleic Acids Research (1995), vol. 23, No. 21, pp. 4407-4414.

Lisitsyn, et al., "Cloning the Differences Between Two Complex Genomes," Science (1993), vol. 259, pp. 946-951.

Nelson, et al., "Genomic mismatch scanning: a new approach to genetic linkage mapping," Nature Genetics (1993), vol. 4, pp. 11-18.

Lisitsyn, et al, "Direct isolation of polymorphic markers linked to a trait by genetically directed representational difference analysis," Nature Genetics (1994), vol. 6, pp. 57-63.

Stubbs, et al., "Differentiation of the spoilage yeast *Zygosaccaromyces bailii* from other *Zygosaccharomyces* species using 18S rDNA as target for a non-radioactive ligase detection reaction," Letters in Applied Microbiology (1994), vol. 19, pp. 268-272.

Gerry, et al., "Universal DNA Microarray Method for Multiplex Detection of Low Abundance Point Mutations," J. Mol. Biol. (1999), vol. 292, pp. 251-262.

Yamanishi, et al., "Ligase chain reaction (LCR)," Human Cell (1993), vol. 6, No. 2, pp. 143-147 (published in Japanese with English abstract).

Wiedmann, et al., "Ligase Chain Reaction (LCR)—Overview and Applications," PCR Methods and Applications (1994), vol. 3, pp. 551-564.

Muth, et al., "Fast capillary electrophoresis-laser induced fluorescence analysis of ligase chain reaction products: Human mitochondrial DNA point mutations caused Leber's hereditary optic neuropathy," Electrophoresis (1996), vol. 17, pp. 1875-1883.

Wilson, et al., "Needle-in-a-haystack detections and identification of base substitution mutations in human tissues," Mutation Research Genomics (1999), vol. 406, pp. 79-100.

Abravaya, et al., "Detection of point mutations with a modified ligase chain reaction (Gap-LCR)," Nucleic Acids Research (1995), vol. 23, No. 4, pp. 675-682.

Jou, et al., "Deletion Detection in the Dystrophin Gene by Multiplex Gap Ligase Chain Reaction and Immunochromatographic Strip Technology," Human Mutation (1995), vol. 5, pp. 86-93.

Andersson et al., 1996, Anal Biochem, 236:107.

Ausubel et al., supra 1992, pp. 1-22 to 1-23.

Banks et al, 1999, J. Biol. Chem. 274:16536.

Bebendck & Kunkel, 1989, Nucleic Acids Res. 17:5408.

Biotechniques, 1991 ISSN 0736-6205 Eaton Pub Co.V.10(1) p. 24-26.

Biotechniques, 1993 ISSN 0736-6250 Eaton Pub Co.V.14(2) p. 214-217.

Blackwell & Weintraub, 1990, Science 250: 1104.

Chamberlain et al., 1988 Nucl. Acids Res. 16:11141.

Cohen & Curran, 1990, Oncogene 5:929.

Cohen et al., 1992, Science 257:1951.

Cotter et al., 1990, Genomics 7:257.

Desmarais et al, 1998, Nucl. Acids Res. 26:1458.

Dramanac et al., 1998, Nature Biotechnology 16:54.

Drmanac et al., 1993, Science, 260(5114) 1649.

Erez-Alon et al, 1998, Cancer Res,58:5447.

Ellsworth et al., 1993, Biotechniques, 14:215.

Farlow et al., 1998, Neurology 50:669.

Feigon et al, 1996, Chem. Biol. 3:611.

Gelfand et al; 1990, PCR Protocols: A Guide to Methods and Applications, Academic Press, San Diego, CA.

Gondo, 1995, Electrophoresis, 16:168.

Hale and Schimmel, 1996, Proc. Natl. Acad. Sci. U.S.A., 93:2755.

Hardenbol & Van Dyke, 1996, Proc. Nat. Sci., U.S.A. 93:2811.

Hatada et al., 1991, Proc. Nat. Acad. Sci. USA 88:9523.

Hayashizaki et al., 1992 Genomics 14:733.

Hou et al, 1996, Nucl. Acids Res. 24:2196.

Hu et al., 1995 PCR Methods and Applications 4:346.

Hubank & Schatz, 1994, Nucl. Acids Res., 22:5640.

Hultman & Uhlen, 1994, J. Biotechnol. 30:35:229.

Kafatos et al., 1979, Nucl. Acids RES., 7:1541.

Keen et al., 1991, Trends Genet., 7:5.

Kohmer et al. 1989, Nucl. Acids Res. 17:7779.

Kuhn et al., 1999, J. Mol. Biol. 286:1337.

Kunkel et al., 1987, Meth. Enzymol., 154:367;2.

Kunsch et al, 1992, Mol. Cell. Biol. 12:4412.

Landegren et al., 1988, Science 241:1077.

Leary et al., 1991, Gene 106:93; 1.

Ledbetter et al., 1991, Genomics 8:475-481.

Listsyn et al., 1993, Science, 259:946.

Liu et al., 1998 Nucleic Acids Res. 26,:1396.

Lukyanov et al., 1996, Nucl. Acids Res.:24:2194.

Mavrothalassitis et al., 1990, DNA Cell Biol., 9:783.

Maxam et al., 1977, Proc. Natl. Acad. Sci. U.S.A., 74-560.

Melton et al., 1984 Nucleic Acids Res. 12:7035.

Mullis & Faloona 1987 Meth. Enzymol, 155:335.

Nelson et al., 1989, Proc. Natl. Acad. Sci. U.S.A. 86:6686.

Newton et al., 1989, Nucleic Acids Res. 17:2503.

Nickerson et al., Proc. Natl. Sci. USA 87:8923.

Noren et al., 1990 Nucleic Acids Res, 18:83.

O'Donovan et al., 1998, Genomics 52:44.

Ophoff et al., 1996, Cell 87, 543.

Parsons and Heflich 1997, Mutat. Res. 374:277.

Pastinen et al., 1997 Genome Res. 7:606.

Ratilainen et al., Biochemistry, 37:12331.

Rosetti et al, Third Wave Technologies; 1997, Mol. Cell. Probes 11:155.
Sadhu et al., 1992 Genomics 14:728.
Saiki et al., 1986 Nature 324:163.
Sambrook et al., 1989, MMLV Reverse Transcriptase—, Molecular Cloning: A Laboratory manual, second edition, pp. 5.52-5.55, 8.11-8.17, Cold Spring Harbor Press, Cold Spring Harbor NY.
Sanger et al., 1977, Proc. Natl. Acad. U.S.A. 74:12, 5463-5467.
Sanger et al., 1975, J. Mol. Biol., 94:441.
Schweder et al.; 1995, Biotechniques 19:38.
Schans et al., 1969, Anal Biochem. 32:14.
Suzuki, et al, 1996, Nucl. Acids Res., 24:797.
Underhill et al. 1996, Proc. Natl. Acad. U.S.A. 93:196.
Underhill et al. 1997, Virology, 237:307.
Wang et al., 1998, Science 280:1077.
Welsh & McClelland, 1990, Nucl. Acids Res. 18:7213.
White et al., 1992, Genomics, 12:301.
Williams et al., 1990 Nucl. Acids Res. 18:6531.
Winzeler et al., 1993, Science 281:1194.
Woodring et al., 1993 Trends Biol. Sci. 18:77.
International Search Report PCT/US00/17404.
T. Ratilainen et al., Hybridization of Peptide Nucleic Acid, Biochemistry vol. 37 pp. 12331-12342 (1998).
D. Nickerson et al., Automated DNA Diagnostics using an ELISA-based oligonucleotide ligation assay, Proc. Nat'l Acad. Sci. vol. 87, pp. 8923-8927 (1990).

* cited by examiner

METHODS OF ENRICHING FOR AND IDENTIFYING POLYMORPHISMS

RELATED APPLICATIONS

This application is a divisional of application Ser. No. 10/391,090, filed Mar. 18, 2003, which is a continuation of U.S. patent application Ser. No. 09/338,855, filed Jun. 23, 1999 The entire teachings of the above applications are incorporated herein by reference.

FIELD OF THE INVENTION

The present invention relates in general to nucleic acid sequence analysis, and in particular to methods which facilitate the identification of sequence polymorphisms.

BACKGROUND OF THE INVENTION

Genomic amplification strategies using the polymerase chain reaction (PCR; Mullis & Faloona, 1987, *Meth. Enzymol.* 155:335) are employed to facilitate the identification of polymorphic sequences. PCR is used to amplify regions of genomic DNA that carry potential polymorphisms. One method hybridizes the PCR products to allele-specific hybridization probes (Saiki et al., 1986, *Nature* 324:163). Other methods utilize oligonucleotide primers that either match or mismatch the targeted polymorphism (Newton et al., 1989, *Nucleic Acids Res.* 17:2503).

With methods that hybridize the PCR product to an allele-specific probe, PCR is used to reduce the complexity of the DNA sample being assayed for the polymorphic marker and to increase the number of copies of the polymorphism-bearing DNA. If 100,000 polymorphic markers were to be assayed per genome, it would be very expensive to perform 100,000 individual PCR reactions. Some advances have been made to multiplex PCR reactions (Chamberlain et al., 1988, *Nucl. Acids Res.* 16:11141), and the degree of multiplexing of the PCR has been scaled up, followed by hybridization to an array of allele-specific probes (Wang et al., 1998, *Science* 280: 1077). However, in the studies by Wang et al., the percentage of PCR products that successfully amplified decreased as the number of PCR primers added to the reaction increased. When approximately 100 primer pairs were used, about 90% of the PCR products were successfully amplified. When the number of primer pairs was increased to about 500, about 50% of the PCR products were successfully amplified. Another disadvantage with multiplex PCR is that individual primer pairs must be synthesized for each polymorphic target. Genotyping DNA with 100,000 polymorphism targets would require, in theory, 200,000 different PCR primers. Not only is the synthesis of such primers costly and time consuming, but not all primer designs succeed in producing a desired PCR product. Therefore considerable time and energy may be spent optimizing the primer designs.

Hatada et al. have cleaved genomic DNA with a rarely cutting restriction enzyme, separated the cleaved DNA by gel electrophoresis, again cleaved the separated DNA with a second restriction enzyme in the gel, and again separated the DNA in a second dimension by electrophoresis (Hatada et al., 1991, *Proc. Natl. Acad. Sci. USA* 88: 9523). According to the Hatada et al. method, one then examines the two-dimensional pattern of DNA spots using DNA from different individuals. Differences in DNA migration patterns result from sequence or nucleotide methylation differences in the restriction enzyme recognition sequences.

Hayashizaki et al. (Hayashizaki et al., 1992, *Genomics* 14:733) use solid-phase adapters specific for restriction fragment ends to physically separate a subset of fragments from genomic DNA. After purification of the adapter-bound DNA fraction away from the rest of the genomic DNA, the bound DNA is separated from the adapters by cleaving again with the restriction enzyme used for the adapter ligation. The DNA released from the adapters is then cloned into a replication vector to make a gene library.

Others have used DNA binding factors to reduce the complexity of populations of synthetic oligonucleotides with stretches of randomized sequences, with the aim of elucidating the consensus binding sequences of the proteins (Mavrothalassitis et al., 1990, *DNA Cell Biol.*, 9:783; Blackwell & Weintraub, 1990, *Science,* 250: 1104; Woodring et al., 1993, *Trends Biol. Sci.*, 18: 77; Hardenbol & Van Dyke, 1996, *Proc. Natl. Acad. Sci. U.S.A.*, 93: 2811).

There is a need in the art for improved methods of identifying polymorphic sequences.

SUMMARY

The invention encompasses a method of enriching for and identifying a nucleic acid sequence difference with respect to a reference sequence comprising: a) contacting a nucleic acid sample with a molecule comprising a sequence-specific binding activity under conditions which permit specific binding, wherein the sample comprises a subset of nucleic acid molecules having a sequence that binds to the sequence-specific binding activity, and wherein a bound subset of nucleic acid molecules is retained by the sequence-specific binding activity, such that the subset of bound nucleic acid molecules is enriched for molecules comprising the sequence recognized by the sequence-specific binding activity; and b) detecting a sequence difference with respect to a reference sequence in the subset of nucleic acid molecules.

In a preferred embodiment of the invention, the molecule comprising sequence-specific binding activity is selected from the group consisting of: transcription factors or DNA binding domains thereof; proteins with zinc-finger DNA binding domains; restriction endonuclease DNA recognition domains; sequence-specific antibodies; oligonucleotides complementary to an adapter ligated to a population of DNA molecules; nucleic acid molecules; aptamers; peptide nucleic acid molecules; peptides; and affinity resins which recognize DNA having a particular G+C content or methylation status.

In a preferred embodiment of the invention, the sequence-specific binding activity is bound to a solid support.

The invention also encompasses a method of identifying nucleic acid sequence differences with respect to a reference sequence comprising: a) cleaving a nucleic acid sample from one or more individuals with one or more sequence-specific cleavage agents to produce nucleic acid fragments; b) operatively linking the fragments of step (a) with molecules capable of being replicated; c) introducing the linked molecules of step (b) into a system capable of replicating only a subset of the linked molecules, and replicating the subset to form a collection of replicated molecules; and d) detecting one or more nucleic acid sequence differences with respect to a reference sequence in the members of the collection of step (c) with a method capable of detecting one or more nucleotide differences with respect to a reference sequence.

In a preferred embodiment, the system capable of replicating the linked molecules comprises host cells and the collection of replicated molecules comprises a library.

In a preferred embodiment, the method capable of detecting one or more nucleotide differences comprises DNA sequencing.

In a preferred embodiment, the method capable of detecting one or more nucleotide differences comprises denaturing HPLC.

In a preferred embodiment, the method capable of detecting one or more nucleotide differences comprises electrophoresis capable of detecting conformational differences in the nucleic acids.

In a preferred embodiment, the method capable of detecting one or more nucleotide differences comprises a protein capable of detecting mismatches between duplexed strands of nucleic acid.

In a preferred embodiment, the sequencing is performed using primers that hybridize to the molecules capable of being replicated.

In a preferred embodiment, the system capable of replicating the linked molecules comprises in vitro replication of the linked molecules.

In a preferred embodiment, the in vitro replication comprises a step utilizing primers for nucleic acid polymerization that hybridize specifically to the molecules capable of being replicated.

In a preferred embodiment, the in vitro replication comprises a step utilizing primers for nucleic acid polymerization that hybridize specifically to sequences comprising both a segment of the molecules capable of being replicated and the fragment ends of a subset of the nucleic acid molecules linked to the molecules capable of being replicated.

In a preferred embodiment, the one or more cleavage agents may be one or more restriction endonucleases. It is preferred that at least one of the restriction endonuclease cleaves DNA infrequently.

In a preferred embodiment, the infrequently cleaving restriction endonuclease is selected from the group consisting of AscI, BssHII, EagI, NheI, NotI, PacI, PmeI, RsrII, SalI, SbfI, SfiI, SgrAI, SpeI, SrfI, and SwaI restriction endonucleases.

The invention also encompasses a method of identifying nucleic acid sequence differences with respect to a reference sequence comprising: a) cleaving a nucleic acid sample from one or more individuals with one or more sequence-specific cleavage agents to produce nucleic acid fragments, wherein the ends of only a subset of the fragments comprise sequences capable of being operatively linked to a separation element; b) operatively linking the subset of step (a) with the separation element; c) separating the linked molecules; and d) detecting one or more nucleic acid sequence differences with respect to a reference sequence in the members of the separated molecules of step (c) with a method capable of detecting one or more nucleotide differences with respect to a reference sequence.

In a preferred embodiment, the method capable of detecting one or more nucleotide differences comprises DNA sequencing.

In a preferred embodiment, the method capable of detecting one or more nucleotide differences comprises denaturing HPLC.

In a preferred embodiment, the method capable of detecting one or more nucleotide differences comprises electrophoresis capable of detecting conformational differences in the nucleic acids.

In a preferred embodiment, the method capable of detecting one or more nucleotide differences comprises a protein capable of detecting mismatches between duplexed strands of nucleic acid.

In a preferred embodiment, the sequencing is performed using primers that hybridize to the sequences capable of being operatively linked to a separation element.

In a preferred embodiment, the one or more cleavage agents are one or more restriction endonucleases. It is preferred that at least one restriction endonuclease cleaves DNA infrequently.

In a preferred embodiment, the infrequently cleaving restriction endonuclease is selected from the group consisting of AscI, BssHII, EagI, NheI, NotI, PacI, PmeI, RsrII, SalI, SbfI, SfiI, SgrAI, SpeI, SrfI, and SwaI restriction endonucleases.

The invention also encompasses a method of enriching for and identifying nucleic acid sequence differences with respect to a reference sequence comprising: a) fragmenting a nucleic acid sample from one or more individuals to an average fragment length; b) physically separating a subset of the nucleic acid fragments generated in step (a) based on the presence or absence of a particular nucleotide sequence within the fragments; c) operatively linking the subset of step (b) with molecules capable of being replicated; d) introducing the linked molecules of step (c) into a system capable of replicating the linked molecules, and replicating the linked molecules to form a collection of replicated molecules; and e) detecting a nucleic acid sequence difference with respect to a reference sequence in the collection of replicated molecules of step (d) using a method capable of detecting one or more nucleotide differences with respect to a reference sequence.

In a preferred embodiment, the system capable of replicating the linked molecules comprises host cells and the collection of replicated molecules comprises a library.

In a preferred embodiment, the method capable of detecting one or more nucleotide differences comprises DNA sequencing.

In a preferred embodiment, the method capable of detecting one or more nucleotide differences comprises denaturing HPLC.

In a preferred embodiment, the method capable of detecting one or more nucleotide differences comprises electrophoresis capable of detecting conformational differences in the nucleic acids.

In a preferred embodiment, the method capable of detecting one or more nucleotide differences comprises a protein capable of detecting mismatches between duplexed strands of nucleic acid.

In a preferred embodiment, the DNA sequencing is performed using primers that hybridize to the molecules capable of being replicated.

In a preferred embodiment, the system capable of replicating the linked molecules comprises in vitro replication of the linked molecules.

In a preferred embodiment, the in vitro replication comprises a step utilizing primers for nucleic acid polymerization that hybridize specifically to the molecules capable of being replicated.

In a preferred embodiment, the in vitro replication comprises a step utilizing primers for nucleic acid polymerization that hybridize specifically to sequences comprising both a segment of the molecules capable of being replicated and the fragment ends of a subset of the nucleic acid molecules linked to the molecules capable of being replicated.

In a preferred embodiment, the in vitro replication is repeated one or more times to increase the enrichment of the linked molecules.

In a preferred embodiment, the method used to physically separate a subset of fragments comprises using a sequence-specific binding molecule.

In a preferred embodiment, the sequence-specific binding molecule is a protein.

In a preferred embodiment, the one or more cleavage agents are restriction endonucleases.

The invention also encompasses a method of enriching for and identifying nucleic acid sequence differences with respect to a reference sequence comprising: a) fragmenting a nucleic acid sample from one or more individuals to an average fragment length; b) separating a subset of the nucleic acid fragments based on the presence or absence of a nucleotide sequence within the fragments; c) detecting one or more nucleic acid sequence differences with respect to a reference sequence in the members of the separated molecules of step (b) with a method capable of detecting one or more nucleotide differences with respect to a reference sequence.

In a preferred embodiment, the method capable of detecting one or more nucleotide differences comprises DNA sequencing.

In a preferred embodiment, the method capable of detecting one or more nucleotide differences comprises denaturing HPLC.

In a preferred embodiment, the method capable of detecting one or more nucleotide differences comprises electrophoresis capable of detecting conformational differences in the nucleic acids.

In a preferred embodiment, the method capable of detecting one or more nucleotide differences comprises a protein capable of detecting mismatches between duplexed strands of nucleic acid.

In a preferred embodiment, the DNA sequencing is performed using primers that hybridize to the molecules capable of being replicated.

In a preferred embodiment, the method used to physically separate a subset of fragments comprises using a sequence-specific binding molecule.

In a preferred embodiment, the sequence-specific binding molecule is a protein.

The invention also encompasses a method of enriching for and identifying nucleic acid sequence differences with respect to a reference sequence comprising: a) hybridizing a nucleic acid sample from one or more individuals with oligonucleotide primers under conditions wherein each of the primers permits extension by a polymerase of two or more different sequences, and wherein the sequences replicated by extension of the primers comprise regions where there are known sequence differences between individuals of the species being examined; b) extending the oligonucleotide primers hybridized in step (a) to form an enriched collection of replicated molecules; and c) detecting one or more nucleic acid sequence differences in the members of the collection with respect to a reference sequence with a method capable of detecting one or more nucleotide differences with respect to a reference sequence.

In a preferred embodiment, the method capable of detecting one or more nucleotide differences comprises DNA sequencing.

In a preferred embodiment, the method capable of detecting one or more nucleotide differences comprises denaturing HPLC.

In a preferred embodiment, the method capable of detecting one or more nucleotide differences comprises electrophoresis capable of detecting conformational differences in the nucleic acids.

In a preferred embodiment, the method capable of detecting one or more nucleotide differences comprises a protein capable of detecting mismatches between duplexed strands of nucleic acid.

In a preferred embodiment, the DNA sequencing is performed using primers that hybridize to the primers hybridized in step (a) and extended in step (b).

In a preferred embodiment, steps (a) and (b) are repeated one or more times to increase the enrichment of the enriched collection of replicated molecules.

In a preferred embodiment, the method further comprises, after step (b) and before step (c) the step of hybridizing a second set of primers that hybridize specifically to sequences comprising both a segment of the first set of primers and a segment of the replicated portion of the molecules generated in step (b).

The invention also encompasses a method of enriching for and identifying nucleic acid sequence differences with respect to a reference sequence comprising: a) fragmenting a nucleic acid sample from one or more individuals; b) physically separating a subset of the nucleic acid fragments based on the size of the fragments; c) operatively linking the subset of step (b) with molecules capable of being replicated; d) introducing the linked subset of molecules of step (c) into a system capable of replicating the linked subset of molecules, and replicating the subset of linked molecules to form an enriched collection of replicated molecules; and e) detecting one or more nucleotide sequence differences in the members of the collection of step (d) with a method capable of detecting one or more nucleotide differences with respect to a reference sequence.

In a preferred embodiment, the system capable of replicating the linked molecules comprises host cells and the collection of replicated molecules comprises a library.

In a preferred embodiment, the method capable of detecting one or more nucleotide differences comprises DNA sequencing.

In a preferred embodiment, the method capable of detecting one or more nucleotide differences comprises denaturing HPLC.

In a preferred embodiment, the method capable of detecting one or more nucleotide differences comprises electrophoresis capable of detecting conformational differences in the nucleic acids.

In a preferred embodiment, the method capable of detecting one or more nucleotide differences comprises a protein capable of detecting mismatches between duplexed strands of nucleic acid.

In a preferred embodiment, the sequencing is performed using primers that hybridize to the molecules capable of being replicated.

In a preferred embodiment, the system capable of replicating the linked molecules comprises in vitro replication of the linked molecules.

In a preferred embodiment, the in vitro replication comprises a step utilizing primers for nucleic acid polymerization that hybridize specifically to the molecules capable of being replicated.

In a preferred embodiment, the in vitro replication is repeated one or more times to increase the enrichment of the collection of replicated molecules.

In a preferred embodiment, the in vitro replication comprises a step utilizing primers for nucleic acid polymerization that hybridize specifically to sequences comprising both a segment of the molecules capable of being replicated and the fragment ends of a subset of the nucleic acid molecules linked to the molecules capable of being replicated.

In a preferred embodiment, the physical separation by size of step (b) is accomplished using electrophoresis, density gradient centrifugation, or centrifugation through a viscous solution.

The invention also encompasses a method of enriching for and identifying nucleic acid sequence differences with respect to a reference sequence comprising: a) fragmenting a nucleic acid sample from one or more individuals; b) physically separating a subset of the nucleic acid fragments based on the size of the fragments; c) detecting one or more nucleic acid sequence differences with respect to a reference sequence in the members of the separated molecules of step (b) with a method capable of detecting one or more nucleotide differences with respect to a reference sequence.

In a preferred embodiment, the method capable of detecting one or more nucleotide differences comprises DNA sequencing.

In a preferred embodiment, the method capable of detecting one or more nucleotide differences comprises denaturing HPLC.

In a preferred embodiment, the method capable of detecting one or more nucleotide differences comprises electrophoresis capable of detecting conformational differences in the nucleic acids.

In a preferred embodiment, the method capable of detecting one or more nucleotide differences comprises a protein capable of detecting mismatches between duplexed strands of nucleic acid.

In a preferred embodiment, the physical separation by size is accomplished using electrophoresis, density gradient centrifugation, or centrifugation through a viscous solution.

The invention also encompasses a method for accessing a sub-portion of a nucleic acid population, such method comprising: a) mixing one or more oligonucleotide primers with a sample of the nucleic acid population under conditions which permit hybridization of one or more primers to the sample, each primer comprising a 3' terminal sequence which hybridizes to an anchor sequence present in the nucleic acid sample; and wherein the one or more oligonucleotide primers contains an additional 3'-terminal extension immediately adjacent to the sequence which hybridizes to an anchor sequence; and b) adding ribonucleotides or deoxynucleotides and a template-dependent polymerizing activity under conditions which permit extension of the one or more oligonucleotide primers, such that the population of extended primers comprises a sub-portion of nucleic acid molecules in the sample.

In a preferred embodiment, the primer comprises an additional 3'-terminal extension immediately adjacent to the sequence which hybridizes to an anchor sequence.

In a preferred embodiment, the additional 3' terminal extension is selected from the group consisting of G, A, T and C.

In a preferred embodiment, the additional 3' terminal extension is selected from the group consisting of: AA; AG; AC; AT; CA; CG; CC; CT; GA; GG; GC; GT; TA; TG; TC; and TT.

In a preferred embodiment, the additional 3' terminal extension is a trinucleotide selected from the group consisting of: AAA; AAC; AAG; AAT; AGA; AGC; AGG; AGT; ACA; ACC; ACG; ACT; ATA; ATC; ATG; ATT; CAA; CAC; CAG; CAT; CCA; CCC; CCG; CCT; CGA; CGC; CGG; CGT; CTA; CTC; CTG; CTT; GAA; GAC; GAG; GAT; GCA; GCC; GCG; GCT; GGA; GGC; GGG; GGT; GTA; GTC; GTG; GTT; TAA; TAC; TAG; TAT; TCA; TCC; TCG; TCT; TGA; TGC; TGG; TGT; TTA; TTC; TTG; and TTT.

In a preferred embodiment, the additional 3' terminal extension is selected from the group consisting of: tetranucleotides, pentanucleotides, hexanucleotides, septanucleotides, and octanucleotides.

In a preferred embodiment, the anchor sequence is the recognition sequence for a sequence-specific DNA binding activity selected from the group consisting of: transcription factors or DNA binding domains thereof; proteins with zinc finger DNA binding domains; restriction endonuclease DNA sequence recognition domains; sequence-specific antibodies; nucleic acid molecules; oligonucleotides complementary to an adapter ligated to a population of DNA molecules; aptamers; peptide nucleic acid molecules; peptides; and affinity resins which recognize DNA having a particular G+C content or methylation status.

In a preferred embodiment, an amount of chain-terminating nucleotide analogs is added sufficient to limit the average extension product to between about 500 and 5000 nucleotides in length.

In a preferred embodiment, an amount of chain-terminating nucleotide analogs is added sufficient to limit the average extension product to approximately 500 nucleotides in length.

In a preferred embodiment, an amount of chain-terminating nucleotide analogs is added sufficient to limit the average extension product to approximately 750 nucleotides in length.

In a preferred embodiment, an amount of chain-terminating nucleotide analogs is added sufficient to limit the average extension product to approximately 1000 nucleotides in length.

In a preferred embodiment, an amount of chain-terminating nucleotide analogs is added sufficient to limit the average extension product to approximately 1500 nucleotides in length.

In a preferred embodiment, an amount of chain-terminating nucleotide analogs is added sufficient to limit the average extension product to approximately 2000 nucleotides in length.

In a preferred embodiment, an amount of chain-terminating nucleotide analogs is added sufficient to limit the average extension product to approximately 3000 nucleotides in length.

In a preferred embodiment, an amount of chain-terminating nucleotide analogs is added sufficient to limit the average extension product to approximately 4000 nucleotides in length.

In a preferred embodiment, an amount of chain-terminating nucleotide analogs is added sufficient to limit the average extension product to approximately 5000 nucleotides in length.

In a preferred embodiment, the anchor sequence is a restriction endonuclease recognition sequence.

In a preferred embodiment, the restriction endonuclease recognition sequence occurs infrequently in the genome of the organism from which the nucleic acid sample is obtained.

In a preferred embodiment, the restriction endonuclease recognition sequence that occurs infrequently in the genome of the organism from which the nucleic acid sample is obtained is selected from the group consisting of: AscI, BssHII, EagI, NheI, NotI, PacI, PmeI, RsrII, SalI, SbfI, SfiI, SgrAI, SpeI, SrfI, and SwaI restriction endonuclease recognition sequences.

In a preferred embodiment, one or more of the oligonucleotides or deoxynucleotides is detectably labeled.

In a preferred embodiment, the label is selected from the group consisting of: fluorescent moieties; radioactive moieties; biotin; and digoxigenin.

In a preferred embodiment, the oligonucleotide primer or primers is/are attached to a solid support or is/are labeled with a moiety allowing attachment to a solid support.

In a preferred embodiment, the method of accessing a sub-portion of a nucleic acid population comprises the additional step of identifying a nucleic acid sequence polymorphism in a population of individuals.

In a preferred embodiment, the method of accessing a sub-portion of a nucleic acid population comprises the additional step of genotyping an individual with respect to a nucleic acid sequence polymorphism.

The invention also encompasses a method for accessing a sub-population of a genome, such method comprising: a) cleaving a nucleic acid sample with a first restriction endonuclease wherein the recognition sequence of the first restriction endonuclease occurs infrequently in the genome; b) ligating an adapter molecule to the cleaved ends generated in step (a), the adapter having an overhang complementary to that generated by the first restriction endonuclease, and ligation of the adapter further fully or partially regenerating the recognition sequence of the first restriction endonuclease; c) mixing an oligonucleotide primer complementary to the adapter molecule, wherein the 3' terminus of the oligonucleotide primer is complementary to the fully or partially regenerated recognition sequence of the first restriction endonuclease, under conditions which permit hybridization of the oligonucleotide primer to the adapter; and d) adding nucleotides and a template-dependent polymerizing activity under conditions which permit extension of the oligonucleotide primer, the resulting population of primer extension products comprising a sub-portion of the molecules in the nucleic acid sample.

The invention also encompasses a method for accessing a sub-population of a genome, such method comprising: a) cleaving a nucleic acid sample with one or more cleavage agents to produce nucleic acid fragments; b) mixing one or more primers capable of annealing to nucleic acid fragment ends generated by the one or more cleavage agents and capable of initiating the replication of the nucleic acid regions comprising the fragment ends under conditions that permit the annealing; c) incubating with a polymerizing activity under conditions that permit extension of the one or more primers, the resulting population of primer extension products comprising a sub-portion of the nucleic acid sequences in the genome, wherein the sub-portion of the nucleic acid sequences comprises an incomplete extension product.

In a preferred embodiment, the one or more cleavage agents are sequence-specific cleavage agents.

In a preferred embodiment, the one or more cleavage agents are sequence-specific cleavage agents and the primers comprise sequences complementary to the recognition sequence of the sequence-specific cleavage agents.

In a preferred embodiment, the primers additionally comprise 3' end sequences capable of hybridizing to only a subset of the molecules in the nucleic, acid sample.

It is preferred that the 3' end sequences comprise terminal extensions immediately adjacent to the sequence that hybridizes to the recognition sequence.

It is also preferred that the terminal extensions are mononucleotides selected from the group consisting of: A, C, G, and T.

It is also preferred that the extensions are dinucleotides selected from the group consisting of: AA; AG; AC; AT; CA; CG; CC; CT; GA; GG; GC; GT; TA; TG; TC; and TT.

It is also preferred that the extensions are trinucleotides selected from the group consisting of: AAA; AAC; AAG; AAT; AGA; AGC; AGG; AGT; ACA; ACC; ACG; ACT; ATA; ATC; ATG; ATT; CAA; CAC; CAG; CAT; CCA; CCC; CCG; CCT; CGA; CGC; CGG; CGT; CTA; CTC; CTG; CTT; GAA; GAC; GAG; GAT; GCA; GCC; GCG; GCT; GGA; GGC; GGG; GGT; GTA; GTC; GTG; GTT; TAA; TAC; TAG; TAT; TCA; TCC; TCG; TCT; TGA; TGC; TGG; TGT; TTA; TTC; TTG; and TTT.

In a preferred embodiment, the extension is selected from the group consisting of: tetranucleotides, pentanucleotides, hexanucleotides, septanucleotides, and octanucleotides.

It should also be appreciated by one skilled in the art that the adapter molecules that are operatively linked to the cleaved ends of nucleic acids may comprise a promoter sequence capable of initiating the synthesis of RNA or DNA from the promoter site with an appropriate polymerase. For example, the adapter may comprise a T7 RNA polymerase promoter oriented so that transcription will proceed into the nucleic acid sample to which the adapter has been operatively linked.

The invention also encompasses a method for accessing a sub-population of a genome, such method comprising: a) cleaving a nucleic acid sample with one or more cleavage agents to produce nucleic acid fragments; b) operatively linking an adapter molecule to the cleaved ends generated in step (a); c) incubating with a polymerizing activity under conditions that permit nucleic acid synthesis from the adapter, the resulting population of extension products comprising a sub-portion of the nucleic acid sequences in the genome, wherein the sub-portion of the nucleic acid sequences comprises an incomplete extension product.

In a preferred embodiment, the adapter molecule contains a transcriptional promoter.

In a preferred embodiment, the adapter molecule contains a free end capable of being extended by a polymerizing activity.

In a preferred embodiment, the adapter molecule is double stranded and contains a sequence capable of being nicked by a second cleavage agent to produce a free end capable of being extended by a polymerizing activity.

The invention also encompasses a method for accessing a sub-population of a genome, such method comprising: a) cleaving a nucleic acid sample with one or more cleavage agents to produce nucleic acid fragments; b) operatively linking an adapter molecule to the cleaved ends generated in step (a); c) mixing a primer complementary to the adapter molecule with the linked molecules generated in step (b) under conditions that permit hybridization of the primer to the adapter; and d) incubating with a polymerizing activity under conditions that permit nucleic acid synthesis from the adapter, the resulting population of primer extension products comprising a sub-portion of the genome, wherein the sub-portion of the genome comprises an incomplete extension product.

In a preferred embodiment, the one or more cleavage agents are sequence-specific cleavage agents.

In a preferred embodiment, the one or more cleavage agents are sequence-specific cleavage agents and the primers comprise sequences complementary to the recognition sequence of the sequence-specific cleavage agents.

In a preferred embodiment, the primers additionally comprise 3' end sequences capable of hybridizing to only a subset of the molecules in the nucleic acid sample.

It is preferred that the 3' end sequences comprise terminal extensions immediately adjacent to the sequence that hybridizes to the recognition sequence.

It is also preferred that the terminal extensions are mononucleotides selected from the group consisting of: A, C, G, and T.

It is also preferred that the extensions are dinucleotides selected from the group consisting of: AA; AG; AC; AT; CA; CG; CC; CT; GA; GG; GC; GT; TA; TG; TC; and TT.

It is also preferred that the extensions are trinucleotides selected from the group consisting of: AAA; AAC; AAG; AAT; AGA; AGC; AGG; AGT; ACA; ACC; ACG; ACT; ATA; ATC; ATG; ATT; CAA; CAC; CAG; CAT; CCA; CCC; CCG; CCT; CGA; CGC; CGG; CGT; CTA; CTC; CTG; CTT; GAA; GAC; GAG; GAT; GCA; GCC; GCG; GCT; GGA; GGC; GGG; GGT; GTA; GTC; GTG; GTT; TAA; TAC; TAG; TAT; TCA; TCC; TCG; TCT; TGA; TGC; TGG; TGT; TTA; TTC; TTG; and TTT.

In a preferred embodiment, the extensions are selected from the group consisting of: tetranucleotides, pentanucleotides, hexanucleotides, septanucleotides, and octanucleotides.

The invention also encompasses a method for accessing a sub-population of a genome, such method comprising: a) cleaving a nucleic acid sample with a cleavage agent; b) operatively linking an adapter molecule to the cleaved ends generated in step (a), the adapter having an end compatible with that generated by the cleavage agent; c) mixing a primer complementary to the adapter molecule, wherein the 3' terminus of the primer is complementary to the recognition sequence of the cleavage agent, under conditions that permit hybridization of the primer to the adapter; and d) adding nucleotides and a template-dependent polymerizing activity under conditions that permit extension of the oligonucleotide primer, the resulting population of primer extension products comprising a sub-portion of the genome.

In a preferred embodiment, the one or more cleavage agents are sequence-specific cleavage agents.

In a preferred embodiment, the one or more cleavage agents are sequence-specific cleavage agents and the primers comprise sequences complementary to the recognition sequence of the sequence-specific cleavage agents.

In a preferred embodiment, the primers additionally comprise 3' end sequences capable of hybridizing to only a subset of the molecules in the nucleic acid sample.

It is preferred that the 3' end sequences comprise terminal extensions immediately adjacent to the sequence that hybridizes to the recognition sequence.

It is also preferred that the terminal extensions are mononucleotides selected from the group consisting of: A, C, G, and T.

It is also preferred that the extensions are dinucleotides selected from the group consisting of: AA; AG; AC; AT; CA; CG; CC; CT; GA; GG; GC; GT; TA; TG; TC; and TT.

It is also preferred that the extensions are trinucleotides selected from the group consisting of: AAA; AAC; AAG; AAT; AGA; AGC; AGG; AGT; ACA; ACC; ACG; ACT; ATA; ATC; ATG; ATT; CAA; CAC; CAG; CAT; CCA; CCC; CCG; CCT; CGA; CGC; CGG; CGT; CTA; CTC; CTG; CTT; GAA; GAC; GAG; GAT; GCA; GCC; GCG; GCT; GGA; GGC; GGG; GGT; GTA; GTC; GTG; GTT; TAA; TAC; TAG; TAT; TCA; TCC; TCG; TCT; TGA; TGC; TGG; TGT; TTA; TTC; TTG; and TTT.

In a preferred embodiment, the extensions are selected from the group consisting of tetranucleotides, pentanucleotides, hexanucleotides, septanucleotides, and octanucleotides.

In a preferred embodiment, an amount of chain-terminating deoxynucleotide analogs is added sufficient to limit the length of the average extension product to between about 500 and 5000 nucleotides.

In a preferred embodiment, an amount of chain-terminating nucleotide analogs is added sufficient to limit the average extension product to approximately 500 nucleotides in length.

In a preferred embodiment, an amount of chain-terminating nucleotide analogs is added sufficient to limit the average extension product to approximately 750 nucleotides in length.

In a preferred embodiment, an amount of chain-terminating nucleotide analogs is added sufficient to limit the average extension product to approximately 1000 nucleotides in length.

In a preferred embodiment, an amount of chain-terminating nucleotide analogs is added sufficient to limit the average extension product to approximately 1500 nucleotides in length.

In a preferred embodiment, an amount of chain-terminating nucleotide analogs is added sufficient to limit the average extension product to approximately 2000 nucleotides in length.

In a preferred embodiment, an amount of chain-terminating nucleotide analogs is added sufficient to limit the average extension product to approximately 3000 nucleotides in length.

In a preferred embodiment, an amount of chain-terminating nucleotide analogs is added sufficient to limit the average extension product to approximately 4000 nucleotides in length.

In a preferred embodiment, an amount of chain-terminating nucleotide analogs is added sufficient to limit the average extension product to approximately 5000 nucleotides in length.

In a preferred embodiment, the oligonucleotide primer or one or more of the deoxynucleotides is detectably labeled. In a preferred embodiment, the label is selected from the group consisting of fluorescent moieties, radioactive moieties, biotin and digoxigenin.

In a preferred embodiment, the oligonucleotide primer is attached to a solid support.

In a preferred embodiment, the method for accessing a sub-population of a genome comprises the additional step of identifying a nucleic acid sequence polymorphism in a population of individuals.

In a preferred embodiment, the method of accessing a sub-population of a genome comprises the additional step of genotyping an individual with respect to a nucleic acid sequence polymorphism.

As used herein, the term "nucleotide sequence" refers to a consecutive linear arrangement of nucleotide bases at least two nucleotides in length on a nucleic acid molecule.

As used herein, the term "reference sequence" refers to a sequence in the genome which is selected as a standard for sequence comparison. The standard is selected based on a sequence containing a nucleotide at one position in the reference sequence or nucleotides at a number of positions in the reference sequence which represent those nucleotides found most frequently at those positions in two or more individuals, or in a population or in a species. A reference sequence also may refer to a sequence selected from an individual and used for comparison to the sequence of another one or more individuals.

As used herein, the term "sequence difference" refers to one or more nucleotide differences in a given sequence with respect to a reference sequence.

As used herein, the term "nucleic acid sample" refers to a sample containing nucleic acid molecules including a sample comprising genomic, cDNA, mitochondrial, chloroplast, or RNA nucleic acids, a sample comprising nucleic acids expressed by a given tissue or cell type, or a sample comprising nucleic acids produced by replication of nucleic acids expressed by a given tissue or cell type. The term "nucleic acid sample" as used herein does not encompass synthetic random sequence DNA or RNA.

As used herein, the term "sequence-specific binding activity" refers to an activity that binds with a particular nucleic acid sequence or sequence motif. Depending upon the particular activity, a sequence-specific binding activity may bind a single, invariant sequence, or it may bind two or more variant sequences with conserved nucleotides at particular positions.

As used herein, the term "separation element" refers to a moiety that can facilitate the separation of a sub-population of nucleic acid molecules from a larger population of nucleic acid molecules based upon recognition of a specific sequence. A separation element according to the invention comprises a sequence-specific binding activity which is either immobilized or capable of being immobilized so as to effect separation of bound nucleic acid molecules.

As used herein, the term "sequence that is bound by a sequence-specific binding activity" refers to the particular sequence or sequence motif bound by a particular sequence-specific binding activity. As used herein, the terms "anchor" or "anchor sequence" and "marker sequence" are equivalent to "sequence that is bound by a sequence-specific binding activity".

According to the invention, such a sequence occurs at least twice, but can occur, for example, 3, 4, 5, 10, 20, 50, 100, 1000, 10,000, 25,000, 50,000 or even 100,000 times or more per genome, and can be selected for or enriched relative to regions of the genome where such sequences are absent or present in lower abundance.

As used herein, the term "enrichment" or "enrichment of genetic markers" refers to the result of any process which increases the concentration of any particular nucleic acid sequence (genetic marker) relative to some other nucleic acid sequence as compared to a sample not subjected to the process. As used herein, a nucleic acid sample is considered to be enriched for a particular marker if the marker is in greater concentration relative to the average concentration of all markers than in a sample which has not been subjected to an enrichment process; for example, where the marker is present in the enriched sample at a concentration 5-fold greater than in the unenriched sample. As used herein, the "complexity" of a DNA sample refers to the number of different unique sequences present in that sample. As used herein, a sample is considered to have "reduced complexity" if it is less complex (for example, in the range of 5-fold to 10-fold, inclusive, less complex) than the DNA sample from which it is derived.

As used herein, "solid support" refers to a solid or semi-solid material which has the property, either inherently or through attachment of some component conferring the property (e.g., an antibody, streptavidin, nucleic acid, or other affinity partner), of binding to a nucleic acid or polypeptide. Such binding can be direct, or may be mediated by a label (e.g., biotin, a nucleic acid sequence tag, or other affinity partner) attached to the nucleic acid or polypeptide. Examples of solid supports include, but are not limited to nitrocellulose and nylon membranes, agarose or cellulose based beads (e.g., Sepharose) and paramagnetic beads.

As referred to herein, the term "cleavage agent" refers to an agent or molecule having an activity that cuts a nucleic acid molecule. It should be understood that a cleavage agent as used herein may cleave one or both strands of a double-stranded nucleic acid molecule.

As used herein, the term "sequence-specific cleavage agent" refers to a cleavage agent that requires or recognizes the presence of a particular nucleic acid sequence, or "recognition sequence" for cleavage to occur. A sequence-specific cleavage agent may cleave the nucleic acid either within the recognition sequence or at a point removed from the recognition sequence on the same molecule.

As used herein, the term "subset of fragments" or "subset of molecules" refers to that fraction of a population of nucleic acid fragments, less than every molecule in the population, having a given characteristic (e.g., having ends capable of annealing to a particular linker or primer, or having a particular average length).

As used herein, the term "sequences capable of being operatively linked" refers to nucleic acid sequences that can be annealed to another particular nucleic acid sequence by Watson:Crick hydrogen bonded base pairing, or annealed and ligated. However, covalent attachment is not always necessary for there to be an operative linkage.

As used herein, the term "molecule capable of being-replicated" refers to a nucleic acid molecule that permits the synthesis or polymerization of copies or replicas of itself or a nucleic acid molecules linked to it. As used in this context, a complementary strand of a nucleic acid falls within the meaning of the term "replica". The term "molecule capable of being replicated" includes, but is not limited to, an oligonucleotide or a plasmid.

As used herein, the term "system capable of replicating said linked molecules" refers to the components (such as oligonucleotide primers and a template-dependent nucleic acid polymerizing activity, or host cells) necessary for in vitro or in vivo generation of a copy or replica of a molecule either annealed or linked to a molecule capable of being replicated.

As used herein, the term "library" refers to a collection of nucleic acid sequences linked to nucleic acid molecules that permit the replication of the members of the collection within host cells.

As used herein, the term "hybridize specifically" means that nucleic acids hybridize with a nucleic acid of complementary sequence. As used herein, a portion of a nucleic acid molecule may hybridize specifically with a complementary sequence on another nucleic acid molecule. That is, the entire length of a nucleic acid sequence does not necessarily need to hybridize for a portion of such a sequence to be considered "specifically hybridized" to another molecule; there may be, for example, a stretch of nucleotides at the 5'-end of a molecule that do not hybridize while a stretch at the 3' end of the same molecule is specifically hybridized to another molecule.

As used herein, the term "infrequently," as applied to cleavage of mammalian DNA (e.g. human DNA) by a restriction endonuclease refers to cleavage which occurs 300,000 times or less in a given genome (for example, 250,000, 200,000, 150,000, or 100,000 times) or which generates an average fragment size of 10,000 bp or more (for example, 20,000 bp, 30,000 bp, 50,000 bp) when a given genomic DNA sample is digested. These frequencies are particularly applicable to human DNA. Restriction endonucleases that generate average fragment sizes of 10,000 base pairs or more on human DNA include, but are not limited to AscI, BssHII, EagI, NheI, NotI, PacI, PmeI, RsrII, SalI, SbfI, SfiI, SgrAI, SpeI, SrfI, and SwaI.

As used herein, the term "frequently," or "more frequently" as applied to cleavage of mammalian DNA by a restriction endonuclease refers to cleavage which occurs more than 300,000 times in a given genome (for example, 500,000-1,000,000 times) or which generates an average fragment size smaller than 10,000 bp (for example, 2,000 bp, 5,000 bp, 8,000 bp) when a given genomic DNA sample is digested. These frequencies are particularly preferred for human DNA.

As used herein, the term "average fragment length" refers to a length of nucleic acid molecules in a particular population of nucleic acid molecules which generally is approximately (i.e., within 50-150% of) a predetermined length. In cases where restriction endonucleases are used to generate fragments of a chosen average fragment length, it should be noted that while the frequency of cutting for a particular sequence may be generally predicted based on the length of the recognition sequence, the base composition of the recognition sequence, and the size or sequence content of the genome, the fragment sizes for a given restriction enzyme may not fall on a bell-shaped curve. In fact, there may be a bimodal or multimodal distribution. For example, the restriction enzyme recognition sequence may happen to occur in a sequence that is highly repeated in the genome. Such an occurrence will cause there to be a "shoulder" in the normal distribution of fragment lengths. Similarly, if the recognition sequence occurs in two different repeated elements, there will be two "shoulders" in the distribution, etc. In practice, the average size of fragments generated by a given restriction endonuclease may be estimated by examination of fragments after electrophoretic separation on a gel. One should recognize, however, that larger fragments stain more intensely than do shorter fragments on such a gel.

As used herein, the term "genotyping an individual with respect to a nucleic acid sequence polymorphism" refers to the identification of the nucleic acid sequence of an individual at a site known to have one or more polymorphisms in a population of other individuals. Within this context a "population of other individuals" can be one or more other individuals.

As used herein, the terms "sub-population of a genome" or "sub-portion of a genome" refer to a collection of nucleic acids derived from a genomic nucleic acid sample wherein the collection does not substantially contain sequences representative of the entire genome.

As used herein, the term "incomplete extension product" refers to the nucleic acid products of primers or promoters extended by a template-dependent nucleic acid polymerizing activity in which polymerization proceeded over less than the full length of the template molecule, or in the case where there is a primer binding site or promoter on both ends of each template, then less than one half of the length of the template molecule. An incomplete extension product may be 10 nt, 20 nt, 100 nt to 5000 nt or more in length, e.g., 100 nt to 1000 nt, 200 nt to 800 nt, 400 nt to 700 nt, or 500 to 600 nt.

The inventive methods provide significant improvements over prior art methods for identifying nucleotide sequence differences which are currently laborious, relatively expensive, and time consuming. Genotyping studies useful for pharmacogenomics studies, for example, may involve 100,000 or more polymorphic markers per study subject. The inventive methods provide simplification of the processes for obtaining such markers and decrease the cost of large-scale genotyping efforts. The invention thus provides for identification of polymorphic markers, but also is applicable to any type of genetic marker, such as (without limitation) tandem repeat sequences, deletions and insertions.

DETAILED DESCRIPTION

The present invention recognizes that a significant problem encountered in the identification of nucleic acid sequence polymorphisms relates to the complexity of the genome. The invention is predicated upon the observation that a nucleic acid marker sequence bound by a sequence-specific binding activity may be used to facilitate the identification of polymorphisms.

The human genome is complex. There are approximately 3 billion nucleotides per haploid human genome. A single polymorphic nucleotide must be identified in the presence of 3 billion other nucleotides, requiring an assay with extreme sensitivity and specificity. The invention provides methods that reduce the complexity of the genome or enrich for a particular subset of sequences that will facilitate the identification of sequence polymorphisms.

The invention disclosed herein recognizes that any nucleic acid sequence bound or recognized by a sequence-specific binding activity may be used to reduce the complexity of the genome to facilitate the identification of polymorphisms. The methods disclosed herein solve the genomic complexity problem by identifying and utilizing a marker sequence that can be enriched for with a simple anchored enrichment procedure. Molecules comprising the marker sequence represent a sub-population of the genome or nucleic acid sample having reduced complexity.

Polymorphisms, particularly single nucleotide polymorphisms ("SNPs"), are essentially randomly distributed throughout the genome. The use of the methods of the invention, through the enrichment for molecules bearing a marker sequence, allows substantially reproducible access to substantially similar reduced-complexity sub-populations in different individuals in a population or even in different samples from a single individual. Because polymorphisms are essentially randomly distributed throughout the genome, a number of polymorphic sequences will be present in the reduced-complexity population of nucleic acid molecules bearing a given marker sequence. Such reduced-complexity sub-populations may then be analyzed to either identify polymorphisms or to determine the genotype of polymorphic loci within that sub-population.

A significant advantage of the methods of the invention is that they permit accession of a substantially similar reduced-complexity sub-population of nucleic acid molecules from any individual in a given species. The reduced-complexity sub-population of nucleic acids may then be genotyped with regard to polymorphisms in the sub-population of nucleic acids using any of a number of methods known in the art. The reduced complexity of the nucleic acid population used for genotype analysis allows for an increased signal to background ratio in the genotyping methods.

For example, a DNA molecule carrying a sequence that can be recognized by a sequence-specific binding molecule, such as the DNA binding protein Gal4, can be separated from DNA not carrying the Gal4 sequence. If such DNA is exposed to Gal4 protein which is bound to a solid support, the DNA molecules carrying the Gal4 binding sequence can be separated from other DNA molecules by washing of the Gal4: DNA complexes to remove unbound DNA. If target genomic DNA is first sheared into sub-genome-sized fragments of a desired size and then subjected to a Gal4 protein separation step, any polymorphic markers contained on the Gal4-bound DNA fragments will be enriched relative to markers on DNA fragments not bound by Gal4 protein. The enriched sub-fraction of the genome (sub-genome) may then be tested for the presence or absence of particular polymorphic alleles through various assays, such as allele-specific hybridization (Saiki, 1986, supra), primer extension (Pastinen et al., 1997, *Genome Res.* 7: 606), the oligonucleotide ligation assay (Nickerson et al., 1990, *Proc. Natl. Acad. Sci. USA* 87: 8923), or the Invader™ assay (Third Wave Technologies; Rosetti et al., 1997, *Mol. Cell. Probes* 11: 155), among others (see below).

Any molecule that binds to a recognition sequence in a nucleic acid can be used to enrich for molecules-bearing a marker sequence. Thus, any sequence bound by a sequence-specific binding activity may be used as a marker according to the invention. For example, DNA binding domains such as found in transcription factors (Jun, Fos, etc.), proteins with zinc-finger DNA binding regions, restriction endonuclease recognition domains, sequence-specific antibodies, nucleic acid molecules, aptamers, peptide nucleic acid (PNA) molecules, peptides and affinity resins that recognize DNA having particular GC content or methylation status may all be used according to the invention.

Marker sequences facilitate the identification of polymorphic sequences. Any sequence variation between a) two individuals, or between b) an individual and a population of individuals or between c) two populations, or between d) one or more individuals and a species as a whole may represent a polymorphism. When compared to sequences within the general population, a polymorphism is typically present at a frequency of about 1% or greater, however the term can apply to any sequence variation between two or more individuals in a population, regardless of the frequency. For example, a polymorphism may be present at a frequency of 0.001% (that is, present in at least one individual per 100,000 individuals), 0.01%, 0.1%, 1% or even 10% or more in a given population of individuals.

A polymorphism may be an insertion, deletion, duplication, or rearrangement of any length of a sequence, including single nucleotide deletions, insertions, or base changes (herein referred to as "single nucleotide polymorphisms" or "SNPs"). A polymorphism, including a SNP, may be neutral or may have an associated variant phenotype. A "neutral polymorphism" is a polymorphism wherein a phenotypic change has not been found in individuals with the sequence variation. A "functional polymorphism" is a sequence variation that has an associated altered phenotype, and typically occurs at a frequency of greater than or equal to 1% in the population. The term "mutation" generally refers to a genetic change that occurs at a frequency of less than or equal to about 1% in a population, and may, but not necessarily, be associated with a phenotypic change.

The inventive methods, i.e., of discovering polymorphisms are useful, for example, in the field of pharmacogenomics, which seeks to correlate the knowledge of specific alleles of polymorphic loci with the way in which individuals in a population respond to particular drugs.

A broad estimate is that for every drug, between 10% and 40% of individuals do not respond optimally. Several well known examples (particularly the association of the response or lack of response to the Alzheimer's drug Tacrine with one's genotype at the ApoE locus (Farlow et al., 1998, Neurology, 50: 669) suggest that allelic differences that affect drug absorption, retention, general metabolism and clearance may be involved in these observed differences.

In order to create a response profile for a given drug, the genotype with regard to polymorphic loci of those individuals receiving the drug must be correlated with the therapeutic outcome of the drug. This is best performed with analysis of a large number of polymorphic loci. Once a genetic drug response profile has been established by analysis of polymorphic loci in a population, a clinical patient's genotype with respect to those loci related to responses to particular drugs must be determined. Therefore, the ability to identify the sequence of a large number of polymorphic loci in a large number of individuals is critical for both establishment of a drug response profile and for identification of an individual's genotype for clinical applications.

Single nucleotide polymorphisms are, by far, the most prevalent form of genetic polymorphism, and as such, they are useful to correlate drug responses with profiles of individual genetic variation to predict patient responses to drugs. The polymorphisms need not necessarily be in genes related to the particular disease being treated with a given drug. Rather, in addition to polymorphisms occurring in disease-related genes, useful polymorphisms for establishing drug response profiles can occur in genes or genetic control elements (enhancers, promoters, processing signals and the like) which ultimately have an effect at any step in the metabolism and clearance of the drug or its metabolites. For that matter, useful polymorphisms may simply be closely genetically linked to a gene or control element involved in a drug response, without actually being a part of the coding or regulatory sequences.

Reduction of the Complexity of Nucleic Acid Samples Using Marker Sequences

In one embodiment, the method of the invention incorporates the use of a complexity reduction mechanism to both produce the DNA to be used to find polymorphic markers and to reduce the complexity of the DNA template prior to genotyping. Thus, polymorphic sequences are discovered using the marker sequence to enrich a subset of the genome, and the same enrichment mechanism is used to reduce the complexity of the genome prior to genotyping. In the following discussion, for clarity, the use of sequence-specific binding molecules according to the invention is described. The sequence specific binding molecules are a pair of cleavage agents, the restriction enzymes NotI and EcoRI, which are representative of a combination of two cleavage agents wherein a first agent cleaves genomic DNA infrequently and a second agent cleaves more frequently than the first.

In a preferred embodiment of the method of the invention, the restriction enzymes NotI and EcoRI are first used to cleave human genomic DNA according to standard methods. The doubly cleaved fragments are then ligated into a NotI/EcoRI cloning vector to produce a sub-library of the human genome. The sub-library consists substantially of the DNA flanking most NotI sites. There are approximately 30,000 NotI sites in the human genome. Thus, a library with 1× representation should contain about 60,000 clones. To discover common polymorphisms in this subset of the genome, one would then sequence 60,000 or more clones from libraries constructed from at least one, and preferably several individuals. The DNA sequencing is performed using vector-specific primers, entering the human DNA from the NotI end and the EcoRI end. If DNA from four individuals is used, for example, one would sequence approximately 60,000×2×4=480,000 segments to achieve a 4× representation around the NotI sites represented in the library. With 4× representation of the NotI/EcoRI sub-genome, one would expect to sequence sample each NotI/EcoRI fragment at least twice for 90.8% of such fragments (1 minus Poisson (0 or 1 with a mean of 4)). One would expect to sample about 57% of the fragments 4 or more times (1 minus Poisson (0, 1, 2, or 3 with a mean of 4)).

Alternatively, one may also make libraries containing NotI/NotI fragments, and sequence both ends of these. Because the NotI recognition sequence is an 8 bp sequence composed entirely of C and G, such fragments are likely to comprise CpG islands found near transcribed regions of the genome. Thus, the subset of the genome represented by libraries made using NotI cleavage will likely be biased towards transcribed regions. An advantage of the this particular method, therefore, is that polymorphisms identified from libraries made using NotI will likely fall near or within protein-encoding sequences.

Methods of the invention that utilize library construction or cloning of enriched sequences to replicate enriched populations require the selection of appropriate vector and host combinations. Vectors and hosts suitable for libraries or other cloning according to the methods of the invention are well known in the art, however preferred attributes of a vector and host for use in the methods of the invention are discussed below.

A sequence selected or enriched according to the methods of the invention may be inserted into a vector in a forward or reverse orientation. A vector may include regulatory sequences, including, for example, a promoter, operably linked to the sequence. A vector may also contain a gene to provide a phenotypic trait for selection of transformed host cells such as dihydrofolate reductase or neomycin resistance for eukaryotic cell culture, or such as tetracycline or ampicillin resistance in *E. coli*. The vector may also include an origin of replication to ensure maintenance of the vector and, if desirable, to provide amplification within the host.

The vector containing the DNA sequence enriched as described herein, as well as an appropriate promoter or control sequence, may be employed to transform an appropriate host. Many suitable vectors and promoters are known to those of skill in the art, and are commercially available. The following vectors are provided by way of example. Bacterial: pQE70, pQE60, pQE-9 (Qiagen), pBS, phagescript, pBluescript SK, pBSKS, LambdaZAP, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia). However, any other plasmids or other vectors may be used as long as they are replicable and viable in the host.

Promoter regions can be selected from any characterized gene and incorporated into appropriate vectors using techniques well known in the art. Bacterial promoters useful according to the invention include, but are not limited to lacI, lacZ, T3, T7, gpt, $\lambda P_R$, $\lambda P_L$ and trp. Eukaryotic promoters include, but are not limited to CMV immediate early, HSV thymidine kinase, early and late SV40, LTRs from retrovirus, and mouse metallothionein-I. Selection of the appropriate vector and promoter is well within the level of ordinary skill in the art.

A host cell may be a higher eukaryotic cell, such as a mammalian cell, or a lower eukaryotic cell, such as a yeast cell, or the host cell may be a prokaryotic cell, such as a bacterial cell. Examples of appropriate hosts include but are not limited to: bacterial cells, such as *E. coli, Bacillus subtilis, Salmonella typhimurium* and various species within the genera *Pseudomonas, Streptomyces,* and *Staphylococcus*, although others may also be employed as a matter of choice; fungal cells, such as yeast; insect cells such as *Drosophila* and Sf9; animal cells such as CHO, COS or Bowes melanoma; plant cells, etc. The selection of an appropriate host is within the scope of one of skill in the art from the teachings herein.

Introduction of the construct into the host cell can be effected by calcium transfection, DEAE-Dextran-mediated transfection, liposome mediated transfection, or electroporation (Ausubel et al., 1992, *Short Protocols in Molecular Biology*, 3rd Edition, John Wiley & Sons, Inc., pp. 9-5 to 9-14) in the case of eukaryotic cells.

Prokaryotic cells may be made competent to take up foreign DNA by standard methods (Ausubel et al., supra, 1992, pp. 1-22 to 1-23) known in the art. Recombinant constructs may be introduced to bacteria by standard transformation (for plasmids) or transfection/infection (for phage DNA or phage particles; see Ausubel et al., supra, 1992, pp. 1-22 to 1-23).

Nucleic Acid Complexity Reduction Methods Useful in the Invention:

The invention contemplates in part the use of complexity reduction and sequence enrichment methods. Complexity reduction reduces the number of unique sequences present in a nucleic acid sample, and enrichment increases the relative concentration of a particular sequence or subset of sequences in a nucleic acid sample.

A subset of nucleic acid molecules, each containing a sequence bound by a sequence-specific binding activity, is prepared as follows according to the invention. Although cleavage agents are used in the following method, other sequence-specific binding activities may be used according to the invention.

The concentration of molecules bearing marker sequences in a population of nucleic acid molecules can be enriched by cleaving genomic DNA with one or more restriction enzymes, and then enriching for a sub-population of the DNA fragments. Genomic DNA can be cleaved with a restriction enzyme, for example SalI, which cleaves somewhat infrequently in genomic DNA. The DNA may then be cleaved with a second restriction enzyme that cleaves more frequently (for example, EcoRI). The doubly-cleaved DNA can then be cloned into a replication vector specific for DNA cleaved by both enzymes (e.g. a Sal I/EcoRI cloning vector). Such cloned DNA will have been enriched for sequences surrounding SalI sites relative to the DNA that was not cloned into the vector.

Alternatively, the SalI ends can be ligated to adapter molecules that specifically hybridize with the SalI sequence overhangs. The DNA may then be sheared, or cleaved with a second restriction enzyme, such as EcoRI. If the adapter molecules are attached to a solid support, or carry a biotin moiety or some other moiety capable of being attached to a solid support, the SalI-terminated fragments may then be separated from the other fragments in the mixture and thus enriched in concentration. Polymorphic markers contained on fragments in such enriched populations of nucleic acid molecules may then be assayed with methods described herein below.

A marker sequence may also be enriched for in a population of nucleic acid molecules by cleaving the nucleic acid (preferably, but not necessarily with a restriction endonuclease; any sequence-specific cleavage agent is acceptable for enrichment according to this method) and then binding (or, alternatively, binding, then cleaving) molecules bearing a marker sequence to a marker sequence-binding activity. Conditions for specific binding, as well as washing conditions for removal of non-specifically bound DNA molecules will necessarily vary depending upon the nature of the DNA binding activity employed and may be adjusted by one of skill in the art. Generally, it is clear that to be selected for this type of use, the sequence specific binding activity and the conditions under which such activity functions will be well known prior to its selection for this purpose.

Another method of enriching for molecules with a particular marker sequence involves the use of non-specific PCR or repeat-sequence PCR. Inter-Alu PCR has been used to amplify a subset of the human genome (Nelson et al., 1989, *Proc. Natl. Acad. Sci. U.S.A.* 86:6686; Sadhu et al., 1992, *Genomics* 14: 728). Primers designed to amplify other repeated sequences, such as SINEs and LINEs have also been made (Cotter et al., 1990, *Genomics* 7:257; Ledbetter et al., 1991, *Genomics* 8: 475-481). Primers that identify such repeated sequences in the genome either amplify all DNA between two points in each amplifiable repeat sequence, or amplify DNA between different adjacent copies of a repeated sequence. Such complexity reduction and enrichment might allow one to detect markers without prior template amplification, however highly repeated sequences such as Alus, SINES, and LINEs are difficult to differentiate from each other. A marker set contained within such repeat elements would be difficult to locate on a physical map. Moreover, certain markers would be located in copies of the repeat element that are identical to other copies in the genome (at least in the region being tested for the presence of the marker), However, markers located between repeat elements would be useful. Primers that would amplify the sequences between repeat elements could be used to enrich a population of nucleic acid molecules for sequences containing useful markers.

DNA amplification using arbitrary PCR primers produces DNA fragments that are mostly unique in sequence (Welsh & McClelland, 1990, *Nucl. Acids Res.* 18:7213; Williams et al., 1990, *Nucl. Acids Res.* 18:6531). Two published methods are respectively called AP-PCR for arbitrarily primed PCR and RAPD for random amplified polymorphic DNA. AP-PCR generally uses longer PCR-primers than RAPD. In both methods, an arbitrary oligonucleotide primer is selected and used to amplify genomic DNA under relatively non-stringent conditions. The primers are extended at multiple locations around the genome, yet yield exponential amplification only in those regions where the primers have hybridized a short distance from another hybridized primer and where both primers are hybridized to opposite strands of the genomic DNA. Multiple arbitrary PCR fragments are produced. The particular fragments are reasonably reproducible from experiment to experiment, provided that similar amplification conditions are used (Schweder et al., 1995, *Biotechniques* 19:38; Ellsworth et al., 1993, *Biotechniques* 14: 215). The lengths of such fragments have been analyzed by electrophoresis and used as markers for the presence or absence of particular DNA sequences in the genomic template. PCR fragment differences between individuals or between two chromosomes in a single individual result from polymorphic differences in the template regions to which the arbitrary primers bind. Methods involving the simultaneous use of two arbitrary primers have also been reported to yield consistent fragment patterns (Hu et al., 1995, *PCR Methods and Applications* 4:346; Desmarais et al., 1998, *Nucl. Acids Res.* 26:1458).

AP-PCR or RAPD may be used to reduce the complexity of the genome for identification of polymorphisms or for genotyping individuals with respect to the polymorphisms. The major DNA bands seen in a gel electrophoresis of AP-PCR or RAPD products are thought to represent about 15 kilobases of the genome (Desmarais et al., 1998, *Nucl. Acids Res.* 26: 1458). This is an enormous reduction of the complexity of the human genome, with sequences present in 15 kilobases roughly equivalent to about $1/1000$ of the yeast genome, and $1/200,000$ of the human genome. One may thus pool 1000 AP-PCR reactions; the complexity of the resulting product would be about equivalent to the yeast genome. In addition, one may perform less stringent AP-PCR reactions or multiplex the AP-PCR reactions, thereby increasing the percentage of the genome being amplified in one reaction. Fragments most abundant in the mix would be the ones amplified most often. Thus, polymorphisms discovered in this reduced-complexity population tend to be those present on the most abundant fragments in the AP-PCR product.

Ideally, AP-PCR conditions may be adjusted (by varying arbitrary primer length, number of primers, and/or annealing conditions) to amplify about $1/200^{th}$ of the human genome in one tube. This product is about as complex as the yeast genome and may be hybridized directly to allele-specific probes using the methods of Winzeler et al., which can detect polymorphisms in the yeast genome without enrichment (Winzeler et al., 1993, *Science* 281: 1194). If common polymorphisms occur with a heterozygosity of approximately 1 in 1500 bases, then approximately 10,000 polymorphisms should be present in such a $1/200^{th}$ sub genome from a single individual. Thus, it is possible to genotype 100,000 polymorphisms using about 10 AP-PCR reactions where approximately $1/200^{th}$ of the genome is being amplified per AP-PCR reaction. Each reaction is then hybridized to an array capable of detecting 10,000 different polymorphisms using the methods of Winzeler et al. This greatly decreases the time and expense required to obtain genotypic data from 100,000 polymorphic markers per individual.

The genotype of an individual with respect to the polymorphic markers found in the NotI/EcoRI (or other similarly constructed) sub-libraries as described above can be determined using the NotI recognition sequence as a marker to generate a reduced-complexity portion of the genome containing known polymorphisms. One way to accomplish this is to cleave genomic DNA with NotI, ligate it to a NotI specific adapter, cleave the DNA with EcoRI, attach the adapter-NotI/RI fragment complexes to a solid support (e.g., via the adapter), wash away unattached DNA, cleave the DNA with NotI and elute the reduced-complexity sample. Such a sample will be about 20 fold less complex than the entire genome. If the entire genome contains 3 billion nucleotides, and there are 30,000 NotI sites, and the average NotI/RI fragment is about 2,500 nucleotides in length, then the NotI/RI fragments will represent about $30,000 \times 2 \times 2500/(3 \times 10^9) = 5\%$ of the genome. Assays used for the detection of these anchored polymorphisms will thus have a 20 fold higher signal to noise ratio than assays used to detect polymorphisms in un-enriched genomic DNA.

Likewise, other methods may be used to reduce the complexity of the genome to a higher degree, proportionately increasing the signal to noise ratio. As noted above, the yeast genome is about 200 fold less complex than the human genome, and it is possible to detect single nucleotide changes in the yeast genome without complexity reduction (Winzeler et al., 1993, supra). Therefore, it is possible to use the NotI/RI complexity-reduction strategy, coupled with a 10 fold linear amplification strategy to produce template DNA of sufficiently low complexity for direct polymorphism detection.

Linear amplification can be carried out in several ways, either coupled with a physical enrichment strategy or performed independently. One method utilizes primers that recognize the NotI adapters (or anchor-specific adapters) that have been ligated to the genomic DNA. If such primers are designed so that they recognize the NotI adapter sequence and, in one embodiment, also recognize the partial NotI sequence that is ligated to the adapter, they can prime DNA synthesis (by any of a number of enzymes known to those skilled in the art) starting at the NotI ends of the genomic DNA. The complexity of the newly synthesized DNA can be further reduced by including a 3'-terminal extension on the primer immediately adjacent to the NotI recognition sequence. Depending upon the length of the extension, different sized subsets of the population will be capable of extension, and thereby enrichment with concomitant reduction in complexity.

For example, a 3'-mononucleotide extension of G, A, T or C immediately adjacent to the sequence complementary to the marker sequence will allow the extension of roughly one quarter of the sequences bearing the marker sequence, for an approximate 4-fold further reduction in complexity. Similarly, a 3'-terminal dinucleotide extension in any of the 16 possible combinations (AA, AC, AG, AT, CA, CC, CG, CT, GA, GC, GG, GT, TA, TC, TG, and TT) will allow extension of roughly ¹⁄₁₆th of the sequences bearing the marker sequence, for an approximately 16-fold further reduction in complexity. By the same reasoning, a 3'-terminal trinucleotide extension in any of the 64 possible combinations (AAA, AAC, AAG, AAT, AGA, AGC, AGG, AGT, ACA, ACC, ACG, ACT, ATA, ATC, ATG, ATT, CAA, CAC, CAG, CAT, CCA, CCC, CCG, CCT, CGA, CGC, CGG, CGT, CTA, CTC, CTG, CTT, GAA, GAC, GAG, GAT, GCA, GCC, GCG, GCT, GGA, GGC, GGG, GGT, GTA, GTC, GTG, GTT, TAA, TAC, TAG, TAT, TCA, TCC, TCG, TCT, TGA, TGC, TGG, TGT, TTA, TTC, TTG and TTT) will effect an approximately 64-fold reduction in complexity. Further reductions may be achieved using 3'-terminal extensions of 4, 5, 6, 7, 8 or more nucleotides immediately adjacent to the sequence complementary to the marker sequence. Using this complexity reduction scheme, one may analyze the entire population, if necessary, through use of primers bearing all 4, 16, 64, 256, etc., possible 3' extensions.

Primer extension products made using, for example, dinucleotide-extended primers, are, in theory, 16 fold less complex than the 5% of the genome selected by the NotI/EcoRI method. Not all of the 16 primers will prime with equal efficiency, and some of the primers will be somewhat promiscuous in their priming (for example when G in the primer or template is opposing T in the template or primer there will be some extension of the primer even though a mismatch occurs between one of the 3' nucleotides of the primer and the template). Overall, however, the primer extension products will be less complex than the NotI/RI subgenome. In this particular case, as well as in cases like it, the primer extension product complexity will be approximately similar to the complexity of the yeast genome, such that the methods of Winzeler, et al. (1993, supra) can be used to detect polymorphisms in the primer extension products. Alternatively, such DNA synthesized from the 16 different primers (used separately) can be used as a template for other polymorphism genotyping methods as referenced herein (see below).

For example, genomic DNA may be cleaved with NotI (or another infrequently cleaving cleavage agent), ligated with a NotI- (or other sequence) specific adapter, and then either used directly for primer extension or further purified. Further purification can be achieved by cleaving the DNA with ECoRI (or other cleavage agent) followed by isolation of the NotI/EcoRI and NotI/NotI fragments using a capture element attached to the NotI adapters (non-limiting examples include a biotin moiety on the adapter and streptavidin on a solid support or a digoxigenin moiety on the adapter and an anti-digoxigenin antibody on a solid support; conditions for capture, as well as methods for biotin or digoxigenin labeling of oligonucleotides are well known to those skilled in the art). The purified subgenome is then mixed with one of 16 different primers bearing 3'-terminal dinucleotide extensions under conditions permitting primer annealing. These primers will anneal to the NotI adapter sequence and the partial NotI recognition sequence ligated to the adapter. However, only in the approximately 1 out of 16 linked molecules bearing the complement of the 3'-terminal dinucleotide extension adjacent to the NotI sequence will an extension product be generated.

The primer-template complexes are then placed into reaction conditions capable of synthesizing DNA (e.g. dNTPs, polymerase, buffer, one set of appropriate conditions is as described herein for PCR, with optimal annealing temperature determined using the formulae also described herein below) and the primers extended from the variable dinucleotide ends to the opposite ends of the template. The primer extension products may be labeled by including one or more labeled dNTPs in the extension reaction. Labels include, but are not limited to radioactive or fluorescent moieties, biotin and digoxigenin. A cycling reaction can be used to linearly amplify the amount of primer extension products, if necessary, for subsequent assays. Labeled primer extension products may then be analyzed for the genotype with respect to particular polymorphisms using, for example, allele-specific hybridization as described herein.

It should be clear to one skilled in the art that purification using some solid phase affinity separation, as outlined above, is not necessary. The DNA can be digested with a cleavage agent, such as NotI, and ligated with specific adapters. Primers specific for the adapters, the NotI site, and in some cases several nucleotides of the genomic sequence adjacent to the NotI site, can be used to create primer extension products that will be enriched for the regions adjacent to the NotI site. The lengths of such primer extension products can be controlled by adding chain terminating nucleotides to the primer extension mix. The ratio of chain terminating nucleotide triphosphates to normal nucleotide triphosphates will influence the average length of primer extension products. Such primer extension products may either be labeled or unlabeled.

These methods allow the complexity of genomic DNA to be significantly reduced simply through cleavage, annealing and/or ligation, DNA capture (optionally), and a small number (in the example cited, 1 to 16) of primer extension reactions. The methods provide subpopulations of the genome that can be directly analyzed for the presence of polymorphisms with lower background and higher efficiency than methods that do not reduce the complexity of the genomic DNA.

Methods of Genotyping Useful in the Invention:

There are a number of methods known in the art that are capable of detecting single nucleotide sequence differences with respect to a reference sequence. Several of these are described below, however it should be understood that any method that allows the determination of the sequence of a particular individual at a particular site may be used to detect sequence differences with respect to a reference sequence in the reduced-complexity nucleic acid populations generated according to the invention.

Direct DNA sequencing according to the classical Sanger (dideoxynucleotide sequencing; Sanger et al., 1975, *J. Mol. Biol.*, 94:441) or Maxam & Gilbert (chemical sequencing; Maxam et al., *Proc. Natl. Acad. Sci. U.S.A.*, 1977, 74:560) methods is capable of detecting nucleotide differences according to the invention. In the Sanger method, a primer that hybridizes to a known sequence on the molecule is extended in the presence of a limiting amount of a chain-terminating nucleoside analog such that a ladder of extension products of different lengths all ending with that nucleotide is generated. Reactions using the same primer with chain-terminating analogs of each of the four dNTPs individually allows determination of the DNA sequence following electrophoresis of the four reactions alongside each other on the same denaturing gel.

Direct DNA sequencing generally requires amplification of the target sequence. However, marker-based nucleic acid sequence enrichment methods as described herein can raise the template concentration to levels where direct sequencing may be effective in determining a single nucleotide sequence difference.

DNA sequencing as necessary for certain embodiments of the invention may also be performed with the Exonuclease Resistance method (Mundy, U.S. Pat. No. 4,656,127), primer-guided microsequencing (Kohmer et al., 1989, *Nucl. Acids Res.*, 17:7779), minisequencing (Pastinen et al., 1997, Genome Res., 7: 606), extension in solution using ddNTJs (Cohen et al., French Patent No. 2,650,840; PCT Application No. WO91/02087), Genetic Bit Analysis™ (GBA; Goelet et al., PCT Application No. 92/15712), ligase-polymerase-mediated GBA (Nifikorbv et al., U.S. Pat. No. 5,679,524) and oligonucleotide ligation assay (OLA; Landegren et al., 1988, *Science* 241:1077) methods as described below.

The exonuclease resistance method (Mundy, supra) involves the use of a primer complementary to the allelic sequence immediately 3' to the polymorphic nucleotide and an exonuclease-resistant nucleotide derivative. The primer is allowed to hybridize to a target molecule contained in a DNA sample obtained from an individual, followed by addition of the exonuclease-resistant nucleotide derivative and a polymerase. If the polymorphic site on the target DNA contains a nucleotide that is complementary to the particular exonuclease-resistant nucleotide derivative, then that derivative will be incorporated into the primer by the polymerase, rendering the primer resistant to nuclease digestion. Because the identity of the nucleotide derivative is known, this method can unambiguously identify the nucleotide present at the polymorphic site.

Microsequencing methods, for example as described by Kohmer et al. (Kohmer et al., supra), involve reactions containing a single labeled deoxynucleotide as the only deoxynucleotide present in the reaction, and a primer complementary to the allelic sequence immediately 3' of the polymorphic site. If the primer becomes labeled upon addition of a polymerase and the labeled deoxynucleotide, the nucleotide present at the polymorphic site must be complementary to that deoxynucleotide.

A variation on the microsequencing method was described by Pastinen and co-workers (Pastinen et al., supra). Briefly, the primers are designed so that their 3' ends hybridize immediately adjacent to each suspected polymorphic site; such primers would comprise sequence specific tags for each polymorphic locus. The primers are then extended with DNA polymerase in the presence of 4 different dideoxynucleoside triphosphates. Each dideoxynucleoside triphosphate is labeled with a different fluorescent molecule. The polymerase is only able to add one nucleotide to each primer, and this identifies the nucleotide in the template immediately adjacent to the 3' end of the primer, and thus the genotype with respect to the polymorphism. The polymerase reactions can be cycled, such as by thermocycling, to increase the amount of product. After the polymerase extension reactions, the primers are then hybridized to a capture array bearing the various sequences containing the polymorphisms. The spots on the capture array will produce fluorescent signal if the primers were extended with a fluorescently labeled dideoxynucleoside triphosphate. The colors emitted from the spots reveal the alleles present in the target nucleic acid sample. The size of the capture array and the number of primers can be increased as needed.

The method using extension in solution and ddNTPs, as described by Cohen et al. (supra) also involves a primer that is complementary to sequences immediately 3' to a polymorphic site. The method determines the identity of the nucleotide of that site using labeled dideoxynucleotide derivatives, which, if complementary to the nucleotide at the polymorphic site will become incorporated onto the terminus of the hybridized primer.

Genetic Bit Analysis™, or GBA™ is described by Goelet et al. (supra). This method is similar to the method of Cohen et al., except that it is preferably a heterogeneous phase assay, in which the primer or the target molecule is immobilized to a solid phase. It is thus easier to perform, more accurate, and better suited for high throughput analyses than the Cohen et al. method.

The Oligonucleotide Ligation Assay or OLA was described by Landegren et al. (supra). This is also a solid phase assay using two oligonucleotides designed to be able to hybridize to abutting sequences of a single strand of a target. One of the oligonucleotides is detectably labeled, and the other is biotinylated. If the precise complementary sequence is found in a target molecule, the oligonucleotides will hybridize such that their termini abut, creating a ligation substrate. Ligation then permits the labeled oligonucleotide to be recovered using avidin or another biotin ligand.

Ligase/Polymerase-mediated genetic bit analysis, described by Nifikorov et al. (supra), involves the immobilization of a first oligonucleotide to a solid substrate. The immobilized oligonucleotide is incubated with a sample containing the target molecule and with a second oligonucleotide capable of hybridizing to the target molecule such that the two oligonucleotides are separated from one another by the polymorphic site. A polymerase, a ligase and one deoxynucleoside triphosphate are added. If the nucleotide at the polymorphic site is complementary to the deoxynucleoside triphosphate added, it will become incorporated by the polymerase and create a ligase substrate. Ligation covalently couples the first oligonucleotide to the second oligonucleotide indicating the identity of the polymorphic base.

In addition to methods that determine the actual sequence of a polymorphic site, other methods can distinguish between alternative sequences based on differing physical characteristics. These include, but are not limited to, dot-blot hybridization, sequencing by hybridization (SBH), denaturing HPLC, electrophoretic methods capable of distinguishing conformationally different nucleic acid molecules, or binding to proteins capable of detecting mismatches between duplexed strands of nucleic acids.

The dot blot method of genotyping with respect to a particular polymorphism involves hybridization analysis using sequence-enriched or amplified DNA (i.e., reduced-complexity DNA) from an individual and oligonucleotide hybridization probes under conditions which allow discrimination of sequences based on single base pair differences. The reduced-complexity DNA is fixed to hybridization membranes using methods appropriate for the specific membrane type chosen (i.e., nitrocellulose, nylon, etc.). Kafatos et al., 1979, *Nucl. Acids Res.*, 7:1541 describe a method suitable for application of DNA samples to nitrocellulose membrane involving alkaline denaturation and binding in high salt. Individual samples of the enriched, immobilized DNA are then hybridized with labeled oligonucleotides, each bearing one allelic form of the polymorphic site, as described below. (A variation of this approach, the "reverse dot blot" method, uses labeled enriched DNA to probe specific polymorphic oligonucleotides immobilized on a substrate.)

Filters bearing reduced-complexity DNA sequences are pre-hybridized in a solution consisting of 5×SSPE (1×SSPE is 180 mM NaCl, 10 mM $NaH_2PO_4$, 1 mM EDTA), 5×Denhardt's solution (1×Denhardt's solution is 0.02% (w/v) polyvinylpyrrolidone, 0.02% (w/v) Ficoll, 0.02% (w/v) BSA, 0.2 mM Tris-HCl, pH8.0, 0.2 mM EDTA), and 0.5% (w/v) SDS for at least 1 h at 55 C. Radiolabeled probe, or probe detectably labeled by other means, is added to the pre-hybridization mixture and incubated at 55° C. for 1 h. Each hybridized filter is then washed twice with 100 ml or more of 2×SSPE, 0.1% SDS for 10 minutes at room temperature. High stringency washes are then performed under temperature and salt conditions such that hybridization is only detected if the probe is 100% complementary to the target sequence. That is, conditions are adjusted so that a single base mismatch will abolish hybridization. Such conditions may be determined by one skilled in the art with a minimum of experimentation necessary for any given polymorphism-containing oligonucleotide. Generally, the hybridization of shorter oligonucleotides (less than or equal to about 25 nt) is destabilized to a greater extent by single base changes than the hybridization of longer ones. One method to achieve the necessary level of specificity with a minimum of experimentation is to maintain the temperature of the washes constant and vary the salt conditions. Lower salt concentrations are more stringent than high concentrations. Specific examples of this type of hybridization being used to determine the genotype of an individual with respect to a polymorphism, and the optimization of stringency are described by Ehrlich et al., in the specification of U.S. Pat. No. 5,604,099.

Following washing, hybridized signal is detected by exposure to X-ray film, or by other appropriate means dependent on the type of label used (i.e., biotin, digoxigenin, etc.). Because hybridization only occurs if the probe and target sequences are 100% complementary, the presence of a hybridization signal with a particular probe directly indicates that the identity of the polymorphic nucleotide is the complement of the corresponding site on the individual probe used. This method may also be adapted to an array format for high throughput analyses.

SBH (Drmanac et al., 1993, *Science*, 260(5114): 1649; Drmanac et al., 1998, Nature Biotechnol., 16: 54) involves a strategy of overlapping block reading. It is based on hybridization of DNA with the complete set of immobilized oligonucleotides of a certain length fixed in specific positions on a support. The efficiency of SBH depends on the ability to effectively sort out perfect duplexes from those that are imperfect (i.e. contain base pair mismatches). This is achieved by comparing the temperature-dependent dissociation curves of the duplexes formed by DNA and each of the immobilized oligonucleotides with standard dissociation curves for perfect oligonucleotide duplexes.

As another example of a method capable of detecting sequence differences based on differing physical characteristics, denaturing high performance liquid chromatography can be used to screen samples for SNPs and other sequence variations (see Ophoff et al., 1996, Cell, 87: 543; Underhill et al., 1996, *Proc. Natl. Acad. Sci. U.S.A.* 93: 196; Underhill et al., 1997, *Virology*, 237: 307; Liu et al., 1998, *Nucleic Acids Res.*, 26: 1396; and O'Donovan et al., 1998, *Genomics*, 52: 44). Alternatively, electrophoretic methods capable of detecting conformational differences in nucleic acids may be used to distinguish polymorphic forms of nucleic acid molecules (see Keen et al., 1991, *Trends Genet.*, 7: 5; White et al., 1992, *Genomics*, 12: 301). As another alternative, one may use a protein capable of detecting mismatches between duplexed strands of nucleic acid (see Parsons & Heflich, 1997, *Mutat. Res.*, 374: 277).

Several embodiments of the invention utilize extension of an annealed primer. This may be accomplished with any of a number of template-dependent polymerases, including, but not limited to Klenow DNA polymerase, Taq DNA polymerase, and AMV or MMLV Reverse Transcriptase. Conditions for primer extension using these polymerases are well known and can be adjusted if necessary for a specific application by one skilled in the art without undue experimentation. See, for example, the following: 1) Klenow DNA polymerase—Kunkel et al., 1987, Meth. Enzymol., 154: 367; 2) Taq DNA polymerase—Gelfand et al., 1990, PCR Protocols: A Guide to Methods and Applications, Academic Press, San Diego, Calif.; and 3) MMLV Reverse Transcriptase—Sambrook et al., 1989, Molecular Cloning: A Laboratory manual, second edition, pp. 5.52-5.55, 8.11-8.17, Cold Spring Harbor Press, Cold Spring Harbor, N.Y.

It should also be appreciated by one skilled in the art that the adapter molecules that are operatively linked to the cleaved ends of nucleic acids may comprise a promoter sequence capable of initiating the synthesis of RNA or DNA from the promoter site with an appropriate polymerase. For example, the adapter may comprise a T7 RNA polymerase promoter oriented so that transcription will proceed into the nucleic acid sample to which the adapter has been operatively linked (U.S. Pat. Nos. 5,716,785 and 5,891,636). When such adapter-linked molecules are exposed to T7 RNA polymerase under the appropriate conditions, an RNA copy of the nucleic acid sample will be created. The length of the RNA products can be controlled by adding chain-terminating ribonucleotide substrates into the reaction mixture in a concentration that will terminate an average transcript at a certain average length. The RNA products themselves, or a cDNA copy of the RNA products, can then be examined for the presence of the polymorphism.

Conditions for in vitro transcription using, for example, T3, T7 or Sp6 polymerase are well known and can be adjusted as necessary for a specific application by one skilled in the art without undue experimentation. See, for example, the following: 1) T3 RNA polymerase—Leary et al., 1991, *Gene.* 106: 93; 2) T7 RNA polymerase—Bebendck & Kunkel, 1989, *Nucleic Acids Res.*, 17: 5408 and Noren et al., 1990, *Nucleic Acids Res.*, 18: 83; and 3) Sp6 RNA polymerase—Melton et al., 1984, *Nucleic Acids Res.* 12: 7035.

EXAMPLES

Example 1

Procedure for the Production of a Human/Lambda Library for Identification of Polymorphisms According to the Invention The following contains an exact step by step description of the procedure utilized in making the four libraries now being used for the identification of SNPs. The procedure being utilized uses lambda ZAP II as the cloning vector. Separate libraries have been made using pBluescript as the cloning vector and other libraries have been made from lambda ZAP II using a slightly different procedure. From the stand-point of the procedure any cloning vector can be used if it contains the suitable restriction enzyme sites. This procedure utilizes both infrequent cutters of the human genome as well as frequent cutters of the human genome.

The procedure is as follows:

1. Lambda Arm Production:

Left Arm Production

The left arm of lambda ZAP II is isolated by the following procedure. Thirty-five μg of lambda ZAP II DNA, in 35 μl of TE buffer (10 mM Tris-HCl, pH 7.5, 1 mM EDTA-Na$_2$) is added to a tube containing 30 μl of 10× Buffer 2 (250 mM NaCl, 100 mM Tris-HCl (pH 7.5), 100 mM MgCl$_2$, 100 mM β-mercaptoethanol, 300 μg/ml Bovine Serum Albumin (BSA), final concentration). To the tube is added 205 μl of doubly distilled (ds) H$_2$O. The solution is mixed by inversion. Finally, 30 μl of the restriction enzyme Hind III (16 Units/μl, 480 U) are added. The solution is then incubated at 37° C. Following 4 hours of incubation, the solution is heated to 68° C. for 15 minutes (min.)

The solution is then extracted twice with an equal volume of phenol followed by extraction once with an equal volume of chloroform. After the extractions, the cut lambda DNA within the solution is precipitated by the addition of 2.5 volumes of ethanol and incubation at minus 20° C. overnight or 20 min in a dry ice acetone bath. The precipitated cut lambda DNA is isolated by centrifugation at 4° C. for 20 min at 14,000-x g. The pelleted cut lambda DNA is then suspended in 75% ethanol and then re-pelleted. Finally, the pelleted cut lambda DNA is dissolved in 140 μl of dsH$_2$O.

The dissolved cut lambda DNA is then cut a second time with a different restriction enzyme by the following procedure. To the 140 μl of cut lambda DNA 10 μl of 10× universal buffer (1 M KOAc, 250 mM Tris-Acetate, pH 7.6, 100 mM MgOAc, 5 mM β-mercaptoethanol, 100 μg/ml BSA, final concentration) and 20 μl of the restriction enzyme Not 1 (8 U/μl, 160 U) is added. The solution is gently mixed by inversion and then incubated at 37° C. for 1 h. Following the incubation, the solution is incubated at 68° C. for 15 min.

The solution is then extracted twice with an equal volume of phenol followed by extraction once with an equal volume of chloroform. After the extractions, the cut lambda DNA within the solution is precipitated by the addition of 2.5 volumes of ethanol and incubation at minus 20° C. overnight or 20 min in a: dry ice acetone bath. The pelleted cut lambda is then resuspended in low TE buffer (5 mM Tris-HCl, pH 7.5 and 0.1 mM EDTA-Na$_2$, final concentration). The resuspended cut lambda is then quantitated using a spectrophotometer, measuring absorbance at 260 nm and 280 nm. The left arm of the lambda vector is now ready for its role in the cloning of human genomic DNA.

Right Arm Production

The right arm of lambda ZAP II is isolated by the following procedure. Thirty-five μg of lambda ZAP II, in 35 μl of TE buffer is added to a tube containing 60 μl of 10× universal buffer and 175 μl dsH$_2$O. After mixing the solution by inversion, 30 μl of the restriction enzyme Mlu I (32 U/μl, 960 U) are added. The solution is then incubated at 37° C. for 4 h. After the incubation, the solution is heated to 68° C. for 15 min.

The solution is then extracted twice with an equal volume of phenol followed by extraction once with an equal volume of chloroform. After the extractions, the cut lambda DNA within the solution is precipitated by the addition of 2.5 volumes of ethanol and incubation at minus 20° C. overnight or 20 min in a dry ice acetone bath. The precipitated cut lambda DNA is isolated by centrifugation at 4° C. for 20 min at 14,000-x g. The pelleted cut lambda DNA is then suspended in 75% ethanol and then re-pelleted. Finally, the pelleted cut lambda DNA is dissolved in 170 μl of dsH$_2$O.

The dissolved cut lambda DNA is then cut a second time with a different restriction enzyme by the following procedure. To the 170 μl of cut lambda DNA 20 μl of 10× universal buffer and 10 μl of the restriction-enzyme EcoRI (24 U/μl, 240 U) is added. The solution is gently mixed by inversion and then incubated at 37° C. for h. Following the incubation, the solution is incubated at 68° C. for 15 min.

The solution is then extracted twice with an equal volume of phenol followed by extraction once with an equal volume of chloroform. After the extractions, the cut lambda DNA within the solution is precipitated by the addition of 2.5 volumes of ethanol and incubation at minus 20° C. overnight or 20 min in a dry ice acetone bath. The pelleted cut lambda is then resuspended in low TE buffer. The resuspended cut lambda is then quantitated using a spectrophotometer, measuring at 260 nm and 280 nm. The right arm is now ready for its role in the cloning of human genomic DNA.

Preparation of Human Genomic DNA for Cloning

Human genomic DNA is prepared for cloning by the following procedure. Twenty μg of human genomic DNA in 20 μl of TE are added to a tube containing 10 μl of universal buffer and 60 μl of dsH$_2$O. Ten μl of the restriction enzyme EcoRI (24 U/μl, 240 U) are added to the tube. The tube is then incubated at 37° C. for 2 h. After the incubation, the following is added to the tube: 42 μl of dsH$_2$O, 5 μl of 10× universal buffer and 3 μl (171 U) of calf intestinal alkaline phosphatase. The tube is then incubated for an additional 30 min at 37° C. Following the incubation, the solution is heated to 68° C. for 15 min.

The solution is then extracted twice with an equal volume of phenol followed by extraction once with an equal volume of chloroform. After the extractions the cut human genomic DNA within the solution is precipitated by the addition of 2.5 volumes of ethanol and incubation at minus 20° C. overnight or 20 min in a dry ice acetone bath. The precipitated, cut human genomic DNA is isolated by centrifugation at 4° C. for 20 min at 14,000×g. The pelleted, cut human genomic DNA is then suspended in 75% ethanol and then re-pelleted. Finally, the pelleted, cut human genomic DNA is dissolved in 70 μl of dsH$_2$O.

The dissolved cut human genomic DNA is then cut a second time with a different restriction enzyme by the following procedure. To the 70 μl of cut lambda DNA 20 μl of 10× universal buffer and 10 μl of the restriction enzyme Not I (8 U/μl, 80 U) are added. The solution is gently mixed by inversion and then incubated at 37° C. for 2 h. Following the incubation, the solution is incubated at 68° C. for 15 min.

The solution is then extracted twice with an equal volume of phenol followed by extraction once with an equal volume of chloroform. After the extractions, the cut human genomic DNA within the solution is precipitated by the addition of 2.5 volumes of ethanol and incubation at minus 20° C. overnight or 20 min in a dry ice acetone bath. The pelleted, cut human genomic DNA is then resuspended in low TE buffer. The resuspended, cut human genomic DNA is then quantitated using a spectrophotometer, measuring absorbance at 260 nm and 280 nm. The digested Human genomic DNA is now ready for its role in the cloning into the vector.

Ligation of the Human Genomic DNA into the Two Lambda ZAP II Arms.

A total of μg of lambda vector arms at a ratio of 1 to 15, left arm to right arm, is mixed with 0.1 μg of the double cut human genomic DNA, 0.5 μl of 10× ligase buffer (500 mM Tris-HCl, pH 7.5, 70 mM MgCl$_2$, 10 mM dithiothreitol), 1 mM rATP, and 0.5 μl of T$_4$ ligase (2 U; Stratagene) in a total volume of 5 μl. The solution is then incubated at 4° C. overnight.

Packaging of the Human/Lambda ZAP II Library.

All procedures used for the packaging of the lambda/human DNA is described within the directions and package insert for the kit as provided by Stratagene.

Preparation of Host Bacteria

The bacterial glycerol stock contained within the kit is used to streak Luria-Bertani agar (LB, Bacto-tryptone 10 g/l, Bacto-yeast extract 5 g/L, NaCl 5 g/l and Bacto-agar 15 g/l). The bacterial glycerol stock contains the *Eschericia coli* strain VCS257. The streaked plates are incubated overnight at 37° C. A single colony is then used to inoculate LB media supplemented with 10 mM MgSO$_4$ and 0.2% (w/v) maltose. The inoculated medium is incubated at 37° C. with shaking for 4-6 h, not past an OD$_{600}$ of 1.0. After incubation, the cells are pelleted by centrifugation at 500-x g for 10 min. The cells are then gently resuspended in half their original volume in 10 mM MgSO$_4$. The cells are now ready for use in the packaging protocol.

Packaging Protocol

The packaging extracts provided with the kit are removed from the minus 80° C. freezer and placed on dry ice. The tube is then quickly thawed by holding the tube between one's fingers. The human/lambda ZAP II DNA ligation mixture (1.7 µl) is added to the packaging extract. The packaging mixture is then stirred with a pipette tip to insure even mixing. The tube is then quickly spun (3-5 seconds). The tube is then incubated at room temperature (22° C.) for 2 hours. After the incubation 500 µl of SM buffer (100 mM NaCl, 8.11 mM MgSO$_4$, 50 mM 1M Tris-HCl (pH 7.5), 0.01% gelatin) is added to the tube. Twenty µl of chloroform is then added to the tube and the contents are mixed. The tube is spun briefly and the supernatant is transferred to a fresh tube. The phage contained within the supernatant are now ready for further usage.

These procedures have been carried out for four separated human genomes. The resulting four human/lambda libraries are being utilized for the detection of SNPs.

Example 2

Procedure by which the Human/Lambda Phage Library is Utilized to Detect Polymorphisms Following is a step by step description of the procedure for the discovery of SNPs within the human genome according to the invention.

Plating and Picking of the Human/Lambda Library

Plaque Plating

XL 2-Blue MRF' *Eschericia coli* cells are maintained as a stock by streaking the cells on LB agar for single colonies. Single colonies are used to inoculate 3 ml LB media. The bacteria are grown at 37° C. for 6 hours with gentle shaking. After-incubation, the bacteria are pelleted (500-x g) and then resuspended in 1.5 ml of 10 mM. MgSO$_4$. These cells are then used for transduction by the human/lambda library. Utilizing the appropriate library phage and the bacterial cells suspended in 10 mM MgSO$_4$, plaque plates are generated as follows: 0.1 ml of the bacterial suspension is mixed with enough library phage to yield between 100 and 300 plaques per 150 mm agar plate. The mixture is incubated at room temperature for 5 min. After the incubation 2.5 ml of pre-warmed LB (37° C.) is added followed by 2.5 ml of molten (45° C.) top agar (10 g/l Bacto-tryptone, 5 g/l Bacto-yeast extract, 5 g/l NaCl and 7 g/l Bacto-agar). This mixture is then immediately poured over a pre-dried LB agar plate (pre-dried for 6-8 h at 37° C.). Initially the plate is incubated right side up at room temperature. After 30 min the plate the plate is placed in a 37° C. incubator bottom side down and incubated for a minimum of 10 h. Plaques begin to appear at 4 hrs. Plates are incubated for no longer than 8 hrs before they are removed from the incubator and placed at 4° C.

Picking Plaques from the Plated Library

Plaques are picked by coring the middle of the plaque using a P200 pipetter and widebore P200 ART tips. Only the top agar is cored and used to make the plaque/phage stocks. Once the plaque is cored, the agar plug is placed in 70 µl of SM buffer containing 5 µl of chloroform. Plaque/phage stocks are maintained in 96-well polystyrene plates. Individual wells are capped and the plate is wrapped in Parafilm™ and stored at 4° C. until they are used. Once a plate has been processed for additional procedures Dimethyl Sulfoxide (DMSO) is added to every well to final concentration of 10%. The plates are then stored at −80° C.

Plaque/phage Polymerase Chain Reaction

The inserted cloned human DNA is next amplified by PCR. Reactions are set up in 96-well formats that replicate the 96-well format of the plaque/phage stock plate. The PCR reactions are 25 µl in total volume and consist of the following 2 µl of plaque/phage stock, 2.5 U of Pfu Turbo, 0.2 mM dATP, 0.2 mM dCTP, 0.2 mM dTTP, 0.1 mM dGTP, 0.1 mM 7-deaza dGTP, 20 mM Tris-HCl (pH 8.8), 10 mM KCl, 10 mM Ammonium sulfate, 0.1% Triton X-100, 0.1 mg/ml BSA and 25 µM primers. The primers being utilized now for PCR are vector specific primers that allow amplification of both the inserted human DNA as well as fragments of the vector. Plaque/phage stocks are run in duplicate with the only difference being the addition of 5% DMSO to one of the duplicate wells. The PCR cycling conditions are as follows: 1 cycle of 98° C. for 3 min; followed by 2 cycles 98° C. for 2 min, 55° C. for 50 sec, 75° C. for 7 min followed by 29 cycles of 95° C. for 50 sec, 58° C. for 50 sec, 75° C. for 7 min, followed by a final elongation at 75° C. for 15 min.

Following PCR, the plus and minus DMSO plates are consolidated into one plate and stored at 4° C.

PCR Reaction Cleanup

PCR products are purified using a 96-well format by employing binding to glass fiber filters in a high salt solution. To each well an equal volume (approximately 50 µl) of binding buffer (4 M guanidine isothiocyanate in 100 mM Tris-HCl (pH 6.4)) is added. The solution (binding buffer and PCR product) is then transferred to the appropriate well of the PCR purification plate. A vacuum is then applied to the PCR purification plate (400 mbar) until all of the liquid has been removed from the wells. The vacuum is then applied for an additional 5 min. After the 5 min. each well is washed with 750 µl of wash buffer (75% ethanol, 2 mM Tris-HCl (pH 6.5), 10 mM NaCl). Vacuum is then again applied to the plate until the wells are dry. Vacuum is applied for an additional 15 min. The PCR purification plate is then centrifuged at 1000-xg for 10 min. The purified PCR product is eluted from the filter by the addition 50 µl of 10 mM Tris-HCl (pH 8.5) to the filter, incubating at room temperature for 5 min, placing a 96-well collection plate underneath the PCR purification plate and centrifuging the plates at 1000xg for 10 min.

Quantitation of the Purified PCR Product

In order to determine which PCR reactions have produced product and to quantitate the amount of purified PCR product present, the fluorescent dye picogreen is used. The procedure is as follows: in a 96-well plate 5 µl of each purified PCR product is placed in the appropriate corresponding well which contains 95 µl of TE. To each appropriate well 100 µl of picogreen, which has been diluted 1 to 200 with TE, is added. The plate is then incubated in the dark for 10 min and then read with the proper spectrofluorometer at the appropriate wavelengths for excitation and emission. Utilizing the proper standards, wells that contain a PCR product can be consolidated into another 96-well plate.

Sequencing of PCR Products

Consolidated, purified PCR products are then cycle-sequenced using BigDye Terminator chemistry (Perkin Elmer/Applied Biosystems). Other types of sequencing chemistries are also compatible with this process. Sequencing is done in a 384 well, format and is carried out as follows: one or 2 µl of the purified PCR product are mixed with 4 µl of the BigDye Ready Reaction Mix, 1 µl of the sequencing primer (either T7 or T3) and enough dsH$_2$O to bring the total reaction volume to 10 µl. Cycle sequencing is then initiated using the following parameters: 25 cycles of 96° C. for 25 sec, 45° C. for 45 sec and 60° C. for 4 min 25 sec. Samples are then precipitated by the addition of 2.5 volumes of 100% ethanol. The samples are incubated at room temperature for 15 min and then centrifuged at 3000×g for 30 min. The plate is then inverted and placed on top of a paper towel and re-centrifuged at 400×g for 1 min. The plates are then allowed to air dry for 15 min at room temperature. The pelleted cycle-sequencing product is then dissolved in 2.5 μl 80% formamide containing a tracking dye and 5 mM EDTA-Na$_2$. Samples are denatured at 96° C. for 2 min and then placed on ice before they are loaded onto the sequencing gel. Sequencing gels are set up and run according to standard procedures specified by the manufacturer Perkin Elmer/Applied Biosystems.

It should be noted that the process of SNP discovery is not limited to the procedures described above.

Example 3

Enriching for and Identifying a Nucleic Acid Sequence Difference With Respect to a Reference Sequence In order to enrich a nucleic acid sample for a subset of nucleic acid molecules bearing a marker sequence, that sample is reacted with a sequence-specific binding activity under conditions that permit specific binding. The sequence specific binding activity can be any activity that binds to a particular sequence or sequence motif. Examples include, but are not limited to transcription factors or their DNA binding domains (e.g., Fos and Jun, see Cohen & Curran, 1990, *Oncogene*, 5: 929) proteins with zinc-finger DNA binding domains (Cohen et al., 1992, *Science* 257: 1951), restriction endonuclease DNA recognition domains, sequence-specific antibodies (Erez-Alon et al., 1998, *Cancer Res.*, 58: 5447), oligonucleotides complementary to an adapter ligated to a population of DNA molecules, nucleic acid molecules, aptamers (Hale & Schimmel, 1996, *Proc. Natl. Acad. Sci, U.S.A.* 93: 2755; Feigon et al, 1996, *Chem. Biol.*, 3: 611), peptide nucleic acid molecules (Kuhn et al., 1999, *J. Mol. Biol.*, 286: 1337; Ratilainen et al., 1998, *Biochemistry.* 37: 12331), peptides (Banks et al., 1999, *J. Biol. Chem.*, 274: 16536) and affinity resins that recognize DNA having a particular G+C content or methylation status.

The binding conditions for the sequence specific binding activity used according to the invention are known by those skilled in the art. That is, the binding conditions will vary with the identity of the particular sequence-specific binding activity selected for use in the method of the invention, but in order for a particular sequence-specific binding activity to be selected for use in this method the conditions for its sequence-specific nucleic acid binding are known in the art.

For example, a DNA binding activity such as the NF-κB p50/p65 complex may be used to select molecules bearing NF-κB recognition sequences under binding conditions as used for protein:nucleic acid binding in the well-known electrophoretic mobility shift assay (Kunsch et al., 1992, *Mol. Cell. Biol.*, 12: 4412).

As another example, a nucleic acid may be used as a sequence-specific binding activity, according to the invention, under conditions known to those skilled in the art to permit specific hybridization or annealing to its complementary sequence. The nucleic acid used as a sequence specific binding activity according to the invention may be a double-stranded molecule having an overhang allowing annealing to molecules with a complementary overhang, or it may be a single-stranded oligonucleotide that hybridizes at a specific marker sequence on a sub-population of nucleic acids in the sample.

In cases where a double-stranded nucleic acid sequence with a specific overhang is used as a sequence-specific binding activity according to the invention, the interaction may be stabilized by the activity of a ligase, such as T4 DNA ligase, under conditions known in the art.

Conditions for hybridization or annealing of a single-stranded nucleic acid as a sequence-specific binding activity are similar to those used for annealing of primers in PCR applications. For example, standard PCR conditions call for annealing primers at a temperature 2° C. to 5° C. below the calculated $T_m$ for a given primer in a buffer comprising 50 mM KCl, 10 mM Tris-HCl (pH 8.4) and 100 mg/ml gelatin (see Gelfand et al., supra). The annealing temperature for a given nucleic acid with its complement may be estimated according to the following formulae, which account for the length, G+C content, and salt conditions in the reaction. For oligonucleotides shorter than 14 bases, use the formula $T_m=2°$ C.(A+T)+4° C.(G+C); for oligonucleotides 14 bases and longer (up to 60-70 nucleotides), use the formula $T_m=81.5+16.6(\log_{10} [Na^+])+0.41(\% G+C)-(600/n)$, where "n" is the chain length. For probes longer than 70 bases, use the formula $T_m=81.5+16.6(\log_{10} [Na^+])+0.41(\% G+C)-(675/n)$. Due to the effects of base stacking, near neighbor effect and buffering capacity, which will vary with the exact oligonucleotide sequence, these formulae give only a close approximation of $T_m$. However, it is well within the capacity of one of ordinary skill in the art to tailor temperatures to a particular oligonucleotide sequence, without undue experimentation, using these formulae as a starting point. Alternatively, a more precise $T_m$ determination may be made using the method of Arnold et al., (U.S. Pat. No. 5,283,174).

The binding activity may be free in solution or attached to a solid support, such as beads or a nylon or nitrocellulose membrane to facilitate the physical separation of protein: nucleic acid complexes from unbound nucleic acids. One of skill in the art may attach binding activities such as proteins (including antibodies), peptides, nucleic acids, aptamers or peptide nucleic acids to solid supports for use with the method of the invention. Attachment may be direct, as is possible for some activities on different types of solid supports (e.g., protein or nucleic acid binding to nitrocellulose or nylon membranes), or indirect, mediated for example by an antibody specific for the sequence specific binding activity or by a molecule, such as streptavidin, which recognizes a labeling moiety, such as biotin, on the sequence-specific binding activity.

As a specific example of the use of a sequence-specific binding activity to enrich for and identify a nucleic acid sequence difference with respect to a reference sequence, one may use the NF-κB p50 DNA binding protein to enrich for DNA molecules containing the consensus sequence 5'-GG-PuNNPyPyCC-3', and the enriched population may be analyzed for sequence differences. To do this, one must take the following steps:

1. Enrich a Genomic DNA Sample for Molecules Bearing the NF-κB Consensus Sequence.

DNA at least 20 μg is incubated with beads bearing immobilized NF-κB p50 protein according to the binding conditions of Kunsch et al. (Kunsch et al., supra). The unbound DNA is removed by washing the beads three times with binding buffer, at ten times the packed volume of the beads per wash. Alternatively, the DNA-binding protein-bearing beads may be made into a column, with DNA being passed over the column in binding buffer. Unbound sequences are then removed by passing several void volumes of binding buffer without DNA over the column.

2. Detect a Nucleic Acid Sequence Difference with Respect to a Reference Sequence.

The bound nucleic acid is eluted, using for example, 300 mM sodium acetate, pH 5.0. Under these conditions, the eluted DNA may be readily concentrated by ethanol precipitation. The DNA, thus enriched for molecules bearing the NF-κB consensus sequence is then ready for further enrichment or for analysis with respect to a reference sequence by any of the genotyping methods described elsewhere herein (e.g., DNA sequencing (including primer-guided microsequencing and minisequencing), exonuclease resistance, extension in solution using ddNTPs, GBA™, ligase-polymerase GBA, OLA, dot-blot/allele-specific hybridization, SBH, denaturing HPLC, electrophoretic methods capable of distinguishing conformational differences between nucleic acids, or binding of proteins capable of detecting mismatches between duplexed strands of nucleic acids. The enrichment protocol will increase the sensitivity and reduce the background in each of these methods.

Example 4

Enriching For and Identifying a Nucleic Acid Sequence Difference With Respect to a Reference Sequence In this example, the sequence specific cleavage agents NotI and EcoRI are used to select molecules bearing sequences near the infrequently occurring NotI sites in the genome. To do so, one will take the following steps:

1) Cleave a DNA sample with NotI and EcoRI. The DNA may be genomic or, for example, cDNA made by reverse-transcription of a total RNA or mRNA sample. Cleavage is performed according to the conditions specified by the supplier of the enzymes.

2) Ligate the sub-population of molecules having both a NotI- and an EcoRI-cleaved end to molecules facilitating their replication. The molecules facilitating replication of the linked DNA may be either an appropriate plasmid cleaved with both NotI and EcoRI (for example, pBluescript II SK, Stratagene), or they may be double-stranded oligonucleotides with overhangs allowing annealing and ligation to the NotI and EcoRI ends of the cleaved DNA. Such oligonucleotides may be free in solution or they may be immobilized on a solid support.

Alternate replication vectors may also be used, such as bacteriophage lambda DNA. For example, Lambda ZAP (Stratagene) is digested with Not I and EcoR I and ligated with the DNA sample. There are several techniques that can be used to enrich for vector containing only fragments with Not I and EcoR I ends. For example, the sample DNA may be cleaved with EcoR I first, then treated with an alkaline phosphatase, such as calf intestinal alkaline phosphatase (Boehringer Mannheim) according to the manufacturer's instructions, to remove 5' phosphates from the sample DNA, then digested with Not I. The Not I/EcoR I digested fragments will be able to ligate with the vector DNA, but EcoR I/EcoR I sample DNA fragments will not be able to ligate with each other, thus reducing the frequency of inserts containing EcoR I/EcoR I fragments.

Another method is to use excess vector having an EcoR I compatible end. For example, Lambda ZAP DNA may be cleaved with Not I and Hind III. Such double digestion leaves a replication-competent left arm of lambda, but cleaves the right arm into multiple fragments. Another preparation of Lambda ZAP DNA may be cleaved with EcoR I and Mlu I. Such double digestion leaves a replication-competent right arm of lambda, but cleaves the left arm into multiple fragments. Since Mlu I cleaves lambda many times in the left arm, and Hind III cleaves lambda many times in the right arm, such double-digested preparations do not efficiently produce replication-competent lambda genomes upon exposure to T4 DNA ligase. Moreover, if both double-digested preparations are mixed together and exposed to T4 DNA ligase, replication-competent lambda genomes are still rare. However if such double-digested preparations are mixed together along with sample DNA that has been digested with Not I and EcoR I, then DNA fragments that have been cleaved at one end by Not I and at the other end by EcoR I will be able to ligate with the functional Not I-cleaved left arm from one lambda preparation and ligate with the functional EcoR I-cleaved right arm from the other lambda preparation to produce replication-competent lambda genomes with reasonably high efficiency. This is provided that the Not I/EcoR I cleaved sample DNA fragments are of appropriate size for lambda replication, which for Lambda ZAP would be fragments up to about 9 kilobases in length. If a fragment with Not I cleavages at both ends, or a fragment with EcoR I cleavages at both ends ligates with one of the lambda arms, it would not be able to ligate with the opposite lambda arm, and thus would form a replication-incompetent product. Since EcoR I cleaves human DNA about 25 times more frequently than does Not I, one can add about 25 times more lambda right arms, as compared with left arms (molar ratio), to the ligation reaction. This will increase the probability that each Not I/EcoR I-cleaved sample fragment will ligate with an EcoR I-cleaved right arm rather than another EcoR I-cleaved sample DNA fragment. Such unwanted ligation of EcoR I-cleaved sample fragments can also be reduced by treatment with an alkaline phosphatase, such as calf intestinal alkaline phosphatase.

Another method to enrich for ligated molecules containing only Not I/EcoR I doubly cleaved sample fragments, is to cleave the sample DNA first with Not I, then ligate the cleaved DNA with a plasmid vector that comprises a Not I and an EcoR I site, but has been cleaved only with Not I. After ligation, the DNA is cleaved with EcoR I, which cleaves both the vector DNA and the sample DNA. Following inactivation of the EcoRI activity, the sample is diluted and ligated using T4 DNA ligase. Diluted DNA preferentially circularizes as opposed to forming bimolecular reactions. Thus there will be a large fraction of circularized plasmids containing Not I/EcoR I cleaved sample DNA.

3) Replicate the Linked Molecules Generated in Step 2.

When the molecules facilitating replication of the linked DNA comprise a plasmid, this comprises the steps of transforming competent host cells (Stratagene) and selecting for transformants according to standard methods.

When the molecules facilitating replication of the linked DNA comprise a lambda genome, this comprises the steps of transfecting host cells and selecting for growth of lambda bacteriophage according to standard methods. Lambda bacteriophage packaging extract (Gigapack™, Stratagene) can be used to greatly increase the efficiency of lambda DNA transfection.

When the molecules facilitating replication of the linked DNA are oligonucleotides or adapters, this comprises the annealing of a primer complementary to one strand of the oligonucleotides or adapters ligated to the NotI cleaved or NotI/EcoRI cleaved DNA fragments and polymerizing the complementary strand of the ligated molecule with a template-dependent DNA polymerizing enzyme (e.g., Klenow DNA polymerase or Taq DNA polymerase; conditions for primer extension with these enzymes and others are well known in the art). Examples of such replication can be found in Lisitsyn et al., 1993, *Science*, 259: 946; Hubank & Schatz, 1994, *Nucl. Acids Res.*, 22: 5640; Hou et al., 1996, *Nucl. Acids Res.*, 24: 2196; Suzuki, et al., 1996, *Nucl. Acids Res.*, 24: 797; and Lukyanov et al., 1996, *Nucl. Acids Res.*, 24: 2194. In order to enrich for those sequences near NotI sites, one uses a primer complementary to the adapter ligated to the NotI ends of the cleaved population. The degree of enrichment may be enhanced by repeating the polymerization reaction. In this regard, thermostable polymerases such as Taq DNA polymerase have the advantage of permitting cycles of annealing and extension, which increases the degree of enrichment with each cycle. Alternatively, strand displacing polymerases can be used to produce multiple copies of the linked DNAs at a single temperature (U.S. Pat. No. 5,744,311).

Alternatively, if a double-stranded oligonucleotide ligated to one end of the cleaved molecules generated in step (1) comprises a transcriptional promoter, such as the bacteriophage T7 promoter, the replication step may comprise the steps of adding RNA polymerase (e.g., T7 polymerase) and ribonucleotides under conditions allowing RNA polymerization from the ligated promoter. Conditions for such in vitro transcription are well known in the art (U.S. Pat. Nos. 5,891,636 and 5,716,785), and the transcripts may be labeled if necessary (labels include, but are not limited to a fluorescent molecule, radioactive molecule, hapten, or biotin). Under optimal conditions, up to 700 moles of transcript can be generated per mole of DNA template, thereby giving as much as a 700-fold enrichment for sequences bearing a ligated promoter.

4) Detect One or More Nucleic Acid Sequence Differences with Respect to a Reference Sequence in the Replicated Population of Molecules.

Detection of nucleic acid sequence differences in the enriched sub-population generated in step (3) is then achieved using any of the genotyping methods described herein. These methods include, for example, DNA sequencing (including primer-guided microsequencing and minisequencing), exonuclease resistance, extension in solution using ddNTPs, GBA™, ligase-polymerase GBA, OLA, dot-blot/allele-specific hybridization, SBH, denaturing HPLC, electrophoretic methods capable of distinguishing conformational differences between nucleic acids, or binding of proteins capable of detecting mismatches between duplexed strands of nucleic acids. The enrichment protocol will increase the sensitivity and reduce the background in each of these methods.

When the in vitro replication system involves transcription from a ligated bacterial promoter, allele-specific (dot-blot) hybridization may be used to detect sequence differences. Alternatively, the ribonuclease protection assay may be used to detect sequence differences in RNA molecules. The method of RNAse protection is well known in the art, and several companies sell kits for the method, including Ambion (RPAII™ kit, Cat. # AM-1410) and Pharmingen (RiboQuant™ kit). The method involves synthesis of an RNA probe from a plasmid bearing a bacteriophage promoter and an insert containing the reference sequence. The RNA probe is then hybridized with the RNA generated in the enrichment protocol. A ribonuclease capable of cleaving single stranded or mismatched duplexes, but not perfectly matched duplexes, is then added. Cleaved duplexes provide evidence of mutations in the sample RNA as compared with the reference RNA. Typically these cleavage products are identified by gelelectrophoresis.

Alternatively, the RNA can be sequenced directly using Sanger sequencing and the enzyme reverse-transcriptase. The RNA may also be converted to cDNA, and then the cDNA may be sequenced.

Example 5

Enriching For and Identifying a Nucleic Acid Sequence Difference With Respect to a Reference Sequence In this example, the sequence specific cleavage agents NotI and EcoRI are used to select molecules bearing sequences near the infrequently occurring NotI sites in the genome. To do so, one will take the following steps:
1) Cleave a DNA Sample with NotI and EcoRI.

The DNA may be genomic or, for example, cDNA made by reverse-transcription of a total RNA or mRNA sample. Cleavage is performed according to the conditions specified by the supplier of the enzymes or as known in the art.
2) Link the Sub-Population of Molecules Having a NotI End to Molecules Facilitating their Separation.

A useful reference for this procedure is Hultman & Uhlen, 1994, *J Biotechnol*, 30:35: 229. The molecules facilitating separation of the molecules with NotI ends may be double-stranded oligonucleotides with NotI-compatible overhangs allowing annealing of the cleaved DNA. The annealed NotI fragments are then ligated to the double-stranded oligonucleotides with ligase under standard conditions. This process will link those sequences near NotI sites to molecules facilitating their separation from those sequences further than the nearest EcoRI recognition sequence from a NotI recognition sequence.
3. Separate the Linked Molecules.

The oligonucleotides may be bound to a solid support at any point before, during or after annealing and ligation of the DNA fragments. In any case, the fragments linked to the oligonucleotides are separated from those not linked to the oligonucleotides by washing the solid support after linkage of the oligonucleotides to the population of fragments. Wash buffer may be a standard buffer such as TE (10 mM Tris pH 8.0, 1 mM EDTA), or any buffer compatible with the solid support and method of oligonucleotide linkage to it.
4. Detect One or More Sequence Differences in the Bound Population with Respect to a Reference Sequence.

Methods of detecting sequence differences appropriate for this enriched population include DNA sequencing, denaturing HPLC, electrophoresis capable of differentiating conformational differences in nucleic acids, and binding to a protein capable of detecting mismatches between duplexed strands of nucleic acid.

Example 6

Enriching for and Identifying Nucleic Acid Sequence Differences with Respect to a Reference Sequence In this example, a sample of nucleic acid is treated to generate fragments that are then bound to a sequence-specific binding activity to effect an enrichment for either those molecules bearing or lacking the sequence bound by that activity. To do so, one must perform the following steps.
1) Fragment a Nucleic Acid Sample to the Chosen Approximate Average Fragment Length.

A nucleic acid sample may be fragmented to facilitate the enrichment for molecules bearing a particular marker sequence. Fragmenting may be accomplished by physical means, such as shearing, or by cleavage with an agent such as a restriction endonuclease. While other cleavage agents are useful according to the invention, restriction endonucleases are particularly useful for several reasons. First, the frequency of cutting for a particular restriction endonuclease, and thereby the average fragment length generated by digestion of a genomic or other DNA sample, is often known or predictable based on the length of the recognition sequence and the nucleotide makeup of the recognition sequence (G/C or A/T-rich, for example). Similarly, the average fragment length for a combination of two or more restriction endonucleases may be predicted. Therefore, DNA may be fragmented to a selected average fragment length by selection of two or more restriction endonucleases of the appropriate known cutting frequencies. It should be noted that there are cases in which a restriction endonuclease will not generate fragments of a size predicted on the basis of the base composition of its recognition sequence. For example, if a recognition sequence for a particular enzyme occurs in a highly repeated segment of DNA, the average number and size of the fragments will be altered relative to a similar sequence not occurring in a repeated element. In practice, the average size of fragments generated by a given restriction endonuclease may be estimated by examination of fragments after electrophoretic separation on a gel. For additional information on the distribution and size fractionation of restricted genomic DNA fragments, see Gondo, 1995, *Electrophoresis.* 16: 168.

Another advantage of fragmenting with restriction endonucleases is that many of the known enzymes cleave so as to generate an overhang on one strand. That overhang may be exploited in subsequent steps. For example, the portion of the cleaved population bound to a sequence specific binding activity may be ligated or annealed to a nucleic acid molecule that permits its cloning to form a library of sequences. Alternatively, the cleaved, bound population may be ligated or annealed to a primer that permits its replication or transcription. The replication or transcription of the molecules bound to the sequence-specific binding activity will further enrich the population and facilitate the detection of sequence differences in the bound subset of nucleic acid molecules with respect to a reference sequence.

2) Physically Separate a Subset of the Nucleic Acid Fragments Generated in Step (1) Based on the Presence or Absence of a Particular Nucleic Acid Sequence.

Fragments bearing a given sequence or sequence motif may be separated from those lacking such a sequence with a sequence-specific binding activity under conditions compatible with sequence-specific binding by that activity (see, for example, Example 3). It should be understood that either the population bearing or the population lacking the particular sequence or sequence motif bound by a sequence-specific binding activity, or both, may be further analyzed as enriched populations.

3) Link the Subset of Nucleic Acid Molecules Physically Separated in Step (2) to Molecules Facilitating the Replication of the Subset.

When the cleavage method used is random, such as, for example, physical shearing, a method such as that taught by Andersson et al. can be used to link the subset of molecules to molecules facilitating their replication (Andersson et al., 1996, *Anal. Biochem.,* 236: 107) Briefly, the method involves enzymatic repair (blunting) of the ends of the sheared molecules, followed by ligation to adapters with 12 bp overhangs. The oligonucleotide adapters used are non-phosphorylated, thus preventing formation of adapter dimers and ensuring efficient ligation of fragments to the adapters. The ligated fragments are then annealed to a modified M13 vector with ends complementary to the adapter overhangs and transformed into bacteria without ligation.

4) Replicate the Subset of Molecules Linked in Step (3).

Linked molecules may be replicated as in Example 4, section 3.

5) Detect a Sequence Difference with Respect to a Reference Sequence.

Detection of sequence differences with respect to a reference sequence may be performed using the same methods indicated in Example 4, section 4, above, or any suitable method known in the art.

Example 7

Enriching For and Identifying Nucleic Acid Sequence Differences With Respect to a Reference Sequence In this example, the sequence specific binding activity is one or more oligonucleotide primers that hybridize to a sequence that occurs at least twice, but can occur for example 3, 4, 5, 10, 20, 50, 100, 1000, 10,000, 25,000, 50,000 or even 100,000 times or more per genome (see AP-PCR, Welsh & McClelland, 1990, supra; and RAPD, Williams et al., 1990, supra). To enrich for and identify nucleic acid sequence differences with respect to a reference sequence according to this method, one must perform the following steps.

1) Hybridize a Nucleic Acid Sample from One or More Individuals with Oligonucleotide Primers.

Conditions for annealing primers, particularly as used in PCR applications, are well known in the art (Gelfand et al., supra). A primer for this particular method may be as short as about five to eight nucleotides, although longer primers are permissible or even preferred in some situations (see below). The number of extension products is a function of the efficiency of annealing under a given set of conditions, and can be manipulated by one of skill in the art to give a desired approximate number of extension products. For example, in general, the annealing temperature is inversely proportional to the number of extension products for a given primer on nucleic acid from a given species. Therefore, the higher the annealing temperature, the fewer the productive extension events. Other factors, such as the makeup of the polymerization buffer or the presence of chain-terminating nucleoside analogs can also be varied to change the makeup of the extended population (see below).

2) Extend the Annealed Oligonucleotide Primers to Form an Enriched Collection of Replicated Molecules.

Extension may be performed with a template-dependent DNA polymerase such as Taq DNA polymerase or Klenow DNA polymerase. Alternatively, extension of an oligonucleotide annealed to an RNA template may be extended with reverse transcriptase.

Annealing and extension may be repeated to increase the degree of enrichment with any of the enzymatic systems described. As noted, however, Taq DNA polymerase has the advantage of allowing multiple cycles of annealing and extension without requiring repeated enzyme addition. It is also noted that the processivity of Taq DNA polymerase is sensitive to the concentration of $Mg^{+2}$ in the reaction, and can be varied by one skilled in the art to vary the characteristics of the extended products.

Under some circumstances (e.g., when one wishes to further limit the complexity of the resulting population, or when one wishes to generate an incomplete extension product), one may add a chain-terminating nucleoside analog to the extension mixture at a concentration that limits the length of the average extension product. Within this embodiment of the invention, one may wish to limit the length of the average extension product to any length between about 500 and 5000 nt. One of skill in the art may determine the concentration of chain-terminating nucleoside analog to add to achieve a given desired average extension product length with a minimum of experimentation.

The extension products may be detectably labeled either by labeling the primer, or by incorporation of labeled nucleotides by the polymerase. Labels of use according to this embodiment of the invention include, but are not limited to fluorescent moieties, radioactive moieties, biotin, and digoxigenin.

Enrichment may also be enhanced by annealing and extending a primer complementary to the original extended primer and repeating the extension steps. The oligonucleotide primer may also have an additional 3'-terminal extension immediately adjacent to the sequence complementary to the selected sequence. This extension, which may be one, two, three, on up to eight nucleotides or more beyond the sequence complementary to the selected sequence, will effect further reduction in the complexity of the population when the primers are extended in the following steps.

3) Detect a Sequence Difference with Respect to a Reference Sequence.

Detection of sequence differences may be accomplished using any of the methods described in Examples 3 or 4, or elsewhere herein, or as known in the art.

Example 8

Enriching For and Detecting a Nucleic Acid Sequence Difference With Respect to a Reference Sequence In this example, a nucleic acid sample is fragmented and a subset of fragments is physically separated on the basis of their size. To perform the method, one must perform the following steps.

1) Fragment a Nucleic Acid Sample from One or More Individuals.

Nucleic acids may be fragmented by any of the methods discussed above.

2) Physically Separate a Subset of the Fragments Based on their Size.

Physical separation of nucleic acid fragments by size may be accomplished in several different ways. First, electrophoretic separation on a gel matrix may be performed according to standard methods using agarose or polyacrylamide gel electrophoresis (see Ausubel et al., supra, pp. 2-13 and 2-23).

Second, fragments may be separated based on their position in a density gradient. CsCl density gradient ultracentrifugation of nucleic acids is a standard method well known in the art. Also, the rate of migration of DNA in a high-density sucrose gradient will vary with the size of the fragment (see, for example, Schans et al, 1969, Anal. Biochem., 32: 14). This is not a function of the density of the DNA, but of the size of the DNA and the effects of viscosity on migration. One may establish a gradient by centrifugation, remove fractions with a fraction collector, and purify nucleic acids of a desired size (evaluated by electrophoresis of a sample from a fraction alongside nucleic acid standard markers).

3) Optionally Linking the Subset of Fragments Isolated on the Basis of their Size to Molecules Facilitating the Replication of the Linked Subset.

Linkage may be performed by annealing and/or ligation of the subset of molecules isolated in step (2) to either a plasmid or to an oligonucleotide as described above in Example 4, section 2.

4) Replicate the Subset of Fragments Linked in Step (3) to Form an Enriched Collection of Replicated Molecules.

Replication may be performed in the same manner as replication of the subset of nucleic acid molecules performed in Example 3.

5) Detect One or More Sequence Differences in the Members of the Enriched Collection Generated in Step (4) with Respect to a Reference Sequence.

Detection of sequence differences is performed according to the same methods as described for Example 8.

Example 9

Accessing a Sub-Portion of a Nucleic Acid Population

In this example, oligonucleotide primers are used to access a sub-portion of a nucleic acid population in order to reduce the complexity of the population and facilitate subsequent analysis (e.g., identification of polymorphisms). An advantage of this method is that it allows reproducible access to a given sub-portion of nucleic acid molecules from the same individual and from different individuals within a given population. To access a sub-portion of a nucleic acid population according to this aspect of the invention, one must perform the following steps.

1. Anneal One or More Oligonucleotide Primers with a Sample of Nucleic Acid.

The oligonucleotide primers used comprise a 3'-terminal sequence complementary to a selected sequence present in the nucleic acid molecules of the sample. The length of the sequence may be varied depending on the size of the sub-portion of the sequences one wishes to access, but will generally be at least about 5' nt in length or longer. The sequence may correspond to any sequence known or predicted to occur in the molecules of the nucleic acid sample. In addition to the sequence complementary to a selected sequence, the oligonucleotide primer may have additional nucleotides 5 of the selected sequence that will facilitate subsequent analysis steps.

The oligonucleotide primer may also have an additional 3'-terminal extension immediately adjacent to the sequence complementary to the selected sequence. This extension, which may be one, two, three, on up to eight nucleotides or more beyond the sequence complementary to the selected sequence, will effect further reduction in the complexity of the population when the primers are extended in the following steps.

According to this embodiment of the invention, the oligonucleotide primers may additionally be attached to a solid support or be labeled with a moiety allowing attachment to a solid support. Methods for attaching oligonucleotides to solid supports are known in the art.

One skilled in the art may determine the annealing conditions for a given oligonucleotide primer or primers in this method (see Example 3). The conditions for annealing will depend on the length and G+C content of the hybrid comprising the selected sequence and its complement in the oligonucleotide primer, plus any 3' terminal extension, and on the salt concentration of the buffer used. Generally, the salt concentration will correspond to the optimal concentration for the template-dependent polymerase chosen for the primer extension step.

2) Extend the Annealed Primer to Generate a Population Comprising a Sub-Portion of the Nucleic Acid Molecules in the Sample.

Extension of the annealed oligonucleotide primers is performed using a template-dependent polymerase such as Taq DNA polymerase or Klenow DNA polymerase under conditions either as specified by the enzyme supplier or as modified by one of skill in the art. Under certain circumstances (e.g., when one wishes to further limit the complexity of the resulting population), one may add a chain-terminating nucleoside analog to the extension mixture at a concentration that limits the length of the average extension product. Within this embodiment of the invention, one may wish to limit the length of the average extension product to any length between about 500 and 5000 nt. One of skill in the art may determine the concentration of chain-terminating nucleoside analog to add to achieve a given desired average extension product length with a minimum of experimentation.

The extension products may be detectably labeled either by labeling the primer, or by incorporation of labeled nucleotides by the polymerase. Labels of use according to this embodiment of the invention include, but are not limited to fluorescent moieties, radioactive moieties, biotin, and digoxigenin.

The sub-portion of the nucleic acid population accessed according to this embodiment of the invention represent a population of reduced complexity that may then be used to identify a nucleic acid sequence polymorphism in a population or in an individual using methods as described elsewhere herein.

Example 10

Accessing a Sub-Population of a Genome

In this example, a sub-population of a genome is accessed in order to reduce the complexity of the genome for subsequent analyses. According to this aspect of the invention, one must take the following steps.

1) Cleave a Nucleic Acid Sample with One or More Cleavage Agents.

The cleavage agent or agents may be sequence-specific cleavage agents, and will preferably cleave infrequently in the genome. Cleavage with a sequence-specific cleavage agent may be performed as described in Example 4, as described elsewhere herein, or in a manner known in the art for a given cleavage agent.

2) Link an Oligonucleotide to the Ends Generated by the Sequence-Specific Cleavage Agent.

Linkage may be by annealing, or by ligation or both. In the case where linkage is by annealing, this step involves addition of either single-stranded oligonucleotides or double-stranded oligonucleotides with a single-stranded overhang capable of annealing to the ends generated by the cleavage agent. It is possible to achieve extension of an oligonucleotide annealed but not ligated to a fragment by way of an overhang.

When an oligonucleotide is ligated, it will be a double-stranded oligonucleotide adapter with an overhang capable of annealing to the fragment ends generated by the cleavage agent. In some instances the annealed oligonucleotide may regenerate the sequence recognized by the sequence-specific cleavage agent. It is also possible to ligate an oligonucleotide adapter comprising a free end or nick capable of being extended by a strand-displacing polymerizing activity. It is also possible to ligate an adapter comprising a sequence capable of being nicked (e.g., an adapter with a mismatched bulge susceptible to cleavage by an enzyme, such as S1 nuclease, that cleaves at mismatched bases).

3) Extend the Oligonucleotide Linked in Step (2).

Extension may be achieved, as noted in step (2) by addition of a nucleic acid polymerizing activity and nucleotides under conditions favored for the particular polymerizing activity used.

Alternatively, extension may be achieved by annealing a single-stranded oligonucleotide complementary to an oligonucleotide ligated in step (2), or complementary to the sequence-specific cleavage agent site regenerated by the ligated sequence, and adding a nucleic acid polymerizing activity and nucleotides under conditions favored for the particular polymerizing activity used. Nucleic acid polymerizing activities may include any template-dependent polymerizing activity, such as, without limitation, Klenow DNA polymerase, Taq DNA polymerase, or an RNA polymerase such as Sp6, T7 or T3 RNA polymerase. In the case of RNA polymerases, the oligonucleotide ligated to the cleaved fragments must comprise a promoter sequence for the selected RNA polymerase.

The extension may be repeated to increase the enrichment of sequences.

In order to generate an enriched sub-portion of the genome by this method, the extension must be limited to avoid the theoretical replication of the entire genome, which would not enrich for sequences near the sites recognized by the sequence-specific cleavage agent. One way to limit the length of the extension products is to include a chosen concentration of chain-terminating nucleotide analogs (such as dideoxynucleotides) to the extension mix. For example, one may add enough of a dideoxynucleotide to limit the average extension product to about 500 nt, 750 nt, 1000 nt, 1500 nt, 2000 nt, 3000 nt, 4000 nt, or even about 5000 nt. For a sequence-specific cleavage agent that gives an average fragment size of 10,000 base pairs or more, this will result in replication of less than half the sequence of the average fragment. That is, the inclusion of one or more chain terminating nucleotide analogs will result in the generation of an incomplete extension product.

Another aspect of this method that will further reduce the complexity of the nucleic acid molecule population is the use of a primer that has a 3'-terminal extension immediately adjacent to the cleavage agent recognition site. This extension, which may be one, two, three, on up to eight nucleotides or more beyond the sequence complementary to the sequence recognized by the cleavage agent, will effect a further reduction in the complexity of the population when the primers are extended. The reduction in complexity effected by the inclusion of 3' terminal extensions on a primer is proportional to the length of the 3'-terminal extension; the longer the extension, the greater the reduction in complexity.

Nucleic acid of reduced complexity generated according to this method may be further analyzed to identify polymorphisms in individuals or in a population of individuals using methods described herein or as known in the art.

I claim:

1. A process to identify in a nucleic acid sample the presence or absence of a nucleic add sequence difference with respect to a reference sequence, the process comprising:
    a) fragmenting nucleic acids in said sample;
    b) linking adapter sequences to the nucleic acid fragments generated in step a;
    c) binding said nucleic acid fragments to a solid support by hybridizing the adapter sequences to complementary oligonucleotides attached to said solid support to form bound nucleic acid fragments, and amplifying said bound nucleic acid fragments to produce bound and amplified fragments, whereby there is enrichment of subsets of the nucleic acid fragments; and
    d) identifying the presence or absence of nucleic acid sequence differences within said bound and amplified fragments with respect to the reference sequence by hybridizing sequencing primers to the bound and amplified fragments and extending the sequencing primers.

2. The process of claim 1 wherein said complementary oligonucleotides act as primers in amplifying said solid support bound nucleic acid fragments.

3. The process of claim 1 wherein the enriched subsets of nucleic acid fragments are at least 5-fold less complex than the original nucleic acid sample.

4. The process of claim 1 wherein the enriched subsets of nucleic acid fragments are at least 10-fold less complex than the original nucleic acid sample.

5. The process of claim 1 wherein there are a plurality of solid supports which each immobilizes separation elements.

6. The process of claim 5 wherein the separation elements are oligonucleotides which bind the nucleic acid fragments to the solid support by hybridizing to the adapter sequences.

7. The process of claim 1 wherein the solid support is beads or a nylon or nitrocellulose membrane.

8. The process of claim 7 wherein the beads are agarose or cellulose or paramagnetic beads.

9. The process of claim 1 wherein the enrichment is of subsets such that the nucleic acid fragments in the subsets have particular lengths.

10. The process of claim 1 wherein sequence differences are identified in at least 10,000 nucleic acid fragments.

11. The process of claim 1 wherein the fragmenting is with restriction enzyme digestion.

12. The process of claim 1 wherein the nucleic acid fragments are amplified before or after step b.

13. The process of claim 1 wherein the adapter sequences are ligated to the nucleic acid fragments in step b.

14. The process of claim 1 wherein the adapter sequences are operatively linked to the nucleic acid fragments in step b.

15. A process to identify in a nucleic acid sample the presence or absence of a nucleic acid sequence difference with respect to a reference sequence, the process comprising:
  a) fragmenting nucleic acids in said sample;
  b) linking adapter sequences to the nucleic acid fragments generated in step a;
  c) binding said nucleic acid fragments to a solid support by hybridizing the adapter sequences to complementary oligonucleotides attached to said solid support to form bound nucleic acid fragments, and amplifying said bound nucleic acid fragments to produce bound and amplified fragments, whereby there is enrichment of subsets of the nucleic acid fragments; and
  d) identifying the presence or absence of nucleic acid sequence differences within said bound and amplified fragments with respect to the reference sequence by hybridizing sequencing primers to the bound and amplified fragments and ligating the sequencing primers to oligonucleotides which are also hybridized to the bound and amplified fragments.

16. The process of claim 15 wherein said complementary oligonucleotides act as primers in amplifying said solid support bound nucleic acid fragments.

17. The process of claim 15 wherein the enriched subsets of nucleic acid fragments are at least 5-fold less complex than the original nucleic acid sample.

18. The process of claim 15 wherein the enriched subsets of nucleic acid fragments are at least 10-fold less complex than the original nucleic acid sample.

19. The process of claim 15 wherein there are a plurality of solid supports which each immobilizes separation elements.

20. The process of claim 15 wherein the separation elements are oligonucleotides which bind the nucleic acid fragments to the solid support by hybridizing to the adapter sequences.

21. The process of claim 15 wherein the solid support is beads or a nylon or nitrocellulose membrane.

22. The process of claim 21 wherein the beads are agarose or cellulose or paramagnetic beads.

23. The process of claim 15 wherein the enrichment is of subsets such that the nucleic acid fragments in the subsets have particular lengths.

24. The process of claim 15 wherein sequence differences are identified in at least 10,000 nucleic acid fragments.

25. The process of claim 15 wherein the fragmenting is with restriction enzyme digestion.

26. The process of claim 15 wherein the nucleic acid fragments are amplified before or after step b.

27. The process of claim 15 wherein the adapter sequences are ligated to the nucleic acid fragments in step b.

28. The process of claim 15 wherein the adapter sequences are operatively linked to the nucleic acid fragments in step b.

* * * * *